United States Patent
Pati et al.

(10) Patent No.: US 6,524,856 B1
(45) Date of Patent: *Feb. 25, 2003

(54) USE OF CONSENSUS SEQUENCES FOR TARGETED HOMOLOGOUS GENE ISOLATION AND RECOMBINATION IN GENE FAMILIES

(75) Inventors: Sushma Pati, Redwood City, CA (US); David A. Zarling, Menlo Park, CA (US); Hong Zeng, Cupertino, CA (US)

(73) Assignee: Pangene Corporation, Fremont, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/209,676

(22) Filed: Dec. 11, 1998

Related U.S. Application Data
(60) Provisional application No. 60/070,734, filed on Dec. 11, 1997.

(51) Int. Cl.$^7$ .................. C12N 15/63; C12N 15/00; C12N 5/00; A01N 63/00; C07H 21/02
(52) U.S. Cl. .................. 435/463; 435/462; 435/455; 435/320.1; 435/325; 536/23.1; 536/23.5; 514/44; 424/93.2
(58) Field of Search .................. 435/183, 440, 435/69.1, 462, 463, 455, 320.1, 325; 536/23.1, 23.5; 424/93.2; 514/44

(56) References Cited

U.S. PATENT DOCUMENTS

| | | |
|---|---|---|
| 5,460,941 A | 10/1995 | Camerini-Otero et al. ..... 435/6 |
| 5,510,473 A | 4/1996 | Camerini-Otero et al. .. 530/23.5 |
| 5,707,811 A | 1/1998 | Ferrin et al. .................. 435/5 |
| 5,731,411 A | 3/1998 | Voloshin et al. ............ 530/326 |

FOREIGN PATENT DOCUMENTS

| | | |
|---|---|---|
| WO | WO93/03868 | 3/1993 |
| WO | WO93/05178 | 3/1993 |
| WO | WO93/22443 | 11/1993 |
| WO | WO93/05223 | 2/1998 |
| WO | WO98/42727 | 10/1998 |

OTHER PUBLICATIONS

Lelias et al FEBS Lett 324(2):127–30, 1993.*
Rigas et al. "Rapid Plasmid Library Screening Using RecA–Coated Biotinylated Probes," (1986) Proc. Natl. Acad. Sci. (U.S.A.) 83: 9591.
Hsieh et al., "Pairing of Homologous DNA Sequences by proteins: Evidence for Three–Stranded DNA," Genes Dev., 4(11)1951–63 (1990).
Sung et al., "Catalysis of ATP–Dependent Homologous DNA pairing and Strand Exchange by Yeast RAD51 Protein," Science 265:1241 (1994).
Baumann et al., "Human RAD51 Protein Promotes ATP–Dependent Homologous Pairing and Strand Transfer Reactions In Vitro," Cell 87:757 (1996).
Dosanjh, et cl., "Isolation and Characterization of RAD51C, a new Human Member of the RAD51 Family of Related Genes," (1998) Nucleic Acid Res. 26:1179–1184.
Cox and Lehman, "Enzymes of General Recombination," Annu. Rev. Biochem., 56:229–62 (1987).
Hsieh and Camerini–Otero "Formation of Joint DNA Molecules by Two Eukaryotic Strand Exchange Proteins Does Not Require Melting of a DNA Duplex," (1989) J. Biol. Chem. 264: 5089.
Howard–Flanders et al. "Role of RecA Protein Spiral Filaments in Genetic Recombination," (1984) Nature 309: 215.
Stasiak et al. "Visualization of RecA–DNA Complexes invo9lved in Consecutive Stages of An In Vitro Strand Exchange Reaction," (1984) Cold Spring Harbor Symp. Quant. Biol. 49: 561.
Register et al. "Electron Microscopic Visualization of the RecA Protein–mediated Pairing and Branch Migration Phases of DNA Stand Exchange," (1987) J. Biol. Chem. 262: 12812).
Cheng et al. "Use of Psoralen–modified Oligonucleotides to Trap Three–stranded RecA–DNA Complexes and Repair of These Cross–linked Complexes by ABC Excinuclease," (1988) J. Biol. Chem. 263: 15110.
Ferrin and Camerini–Otero "Selective Cleavage of Human DNA: RecA–Assisted Restriction Endonuclease (RARE) Cleavage," (1991) Science 354: 1494.
Ramdas et al. "RecA Protein Promoted Homologous Pairing In Vitro," (1989) J. Biol. Chem. 264: 11395.
Strobel et al. "Site–Specific Cleavage of Human Chromosome 4 Mediated by Triple–Helix Formation," (1991) Science 254: 1639.
O'Gorman et al. "Recombinase–Mediated Gene Activation and Site–Specific Integration in Mammalian Cells," (1991) Science 251: 1351.
Onouchi et al. "Operation of an Efficient Site–Specific Recombination System of Zygosaccharomyces rouxii in Tobacco Cells," (1991) Nucleic Acids Res. 19: 6373.
Kucherlapati et al. "Homologous Recombination Between Plasmids in Mammalian Cells can be Enhanced by Treatment of Input DNA," (1984) Proc. Natl. Acad. Sci. (U.S.A.) 81: 3153.
Smithies, O. "Insertion of DNA Sequences into the Human Chromosomal β–globin Locus by Homologous Recombination," (1985) Nature 317: 230.

(List continued on next page.)

Primary Examiner—Scott D. Priebe
Assistant Examiner—Sumesh Kaushal
(74) Attorney, Agent, or Firm—Richard R. Trecartin; Nancy B. Capps; Dorsey & Whitney LLP

(57) ABSTRACT

The invention relates to compositions and methods for targeting sequence modifications in one or more genes of a related family of genes using enhanced homologous recombination techniques. These techniques may be used to create animal or plant models of disease as well as to identify new targets for drug or pathogen screening.

8 Claims, 6 Drawing Sheets

OTHER PUBLICATIONS

Song et al. "Accurate Modification of a Chromosomal Plasmid by Homologous Recombination in Human Cells," (1987) Proc. Natl. Acad. Sci. (U.S.A.) 84: 6820.

Doetschman et al. "Targeted Correction of a Mutant HPRT Gene in Mouse Embryonic Stem Cells," (1987) Nature 330: 576.

Kim and Smithies "Recombinant Fragment Assay for Gene Targeting Based on the Polymerase Chain Reaction," (1988) Nucleic Acids Res. 16: 8887.

Doetschman et al. "Targeted Mutation of the HPRT in Mouse Embryonic Stem Cells," Proc. Natl. Sci. U.S.A., 85(22):8583–7 (1988).

Koller and Smithies, "Inactivating the Beta 2–Microglobulin Locus in Mouse Embryonic Stem Cells by Homologous Recombination," Proc. Natl. Acad. Sci. USA, 86(22):8932–5 (1989).

Shesely et al. "Correction of a Human $\beta^s$–Globin Gene by Gene Targeting," (1991) Proc. Natl. Acad. Sci. (U.S.A.) 88: 4294.

Kim et al. "Problems Encountered in Detecting a Targeted Gene by the Polymerase Chain Reaction," (1991) Gene 103: 227.

Cox and Lehman "Enzymes of General Recombination," (1987) Ann. Rev. Biochem. 56: 229.

Radding, C.M. "Homologous Pairing and Strand Exchange in Genetic Recombination," Annu. Rev. Genet. 16:405–37 (1982).

Madiraju et al. "Properties of a Mutant recA–Encoded Protein Reveal a Possible Role for *Escherichia Coli* recF– Encoded Protein in a Genetic Recombination," (1988) Proc. Natl. Acad. Sci. (U.S.A.) 85: 6592.

McCarthy et al. "Sensitive Homologous Recombination Strand–Transfer Assay: Partial Purification of a *Drosophila melanogaster* Enzyme and Detection of Sequence Effects on the Strand–Transfer Activity of RecA Protein," (1988) Proc. Natl. Acad. Sci. (U.S.A.) 85: 5854.

Lopez et al., "Promotion of Double–Strand Break Repair by Human Nuclear Extracts Preferentially Involves Recombination with Intact Homologous DNA," Nucleic Acids Res., 15(17):6813–26 (1987).

Lopez, et al., "Homologous Recombination Intermediates Between Two Duplex DNA Catalysed by Human Cell Extracts," Nucleic Acids Res., 15(14):5643–55 (1987).

\* cited by examiner

| Gene Family | Motif (#-aa) | Members | Degeneracy |
|---|---|---|---|
| Metabotropic Glutamate Like GPCR | 34-EAM(LF)(YFH) | 22Total 8Human | 256x14mer |
| " | 69-(YH)ALEQ | " | 256x14mer |
| " | 130-IPQI(SA) | " | 432x14mer |
| " | 637-KTN(RC)I | " | 192x14mer |
| " | 745-FNEAK | " | 64x15mer |
| " | 752-FTMYTT | " | 64x17mer |
| Calcitonin Type GPCR | 76-TWDGW | 8Total 2Human | 32x15mer |
| " | 99-YF(PQ)DFD | " | 128x17mer |
| " | 183-CQR(VI)T | " | 256x14mer |
| " | 245-CYNFWM | " | 16x18mer |
| " | 279-GWGFP | " | 128x15mer |
| " | 299-NDNCW(LMI) | " | 48x17mer |
| " | 312-YIIHGP | " | 144x17mer |
| Glucagon Type GPCR | 91-WYLPW | 6Total 2Human | 64x15mer |
| " | 154-YTVGY | " | 256x15mer |
| " | 179-HCTRN | " | 256x15mer |
| " | 413-N(KN)EVQ | " | 128x15mer |
| Vasoactive Intestinal Polypeptide GPCR | 177-KLHCT | 7Total 2Human | 256x15mer |
| " | 249-VEGLYL | " | 512x15mer |
| " | 407-YCFLN | " | 128x15mer |
| Parathyroid Hormone GPCR | 110-YDFNHK | 7Total 2Human | 64x18mer |
| " | 136-TWANY | " | 64x15mer |
| " | 166-YTVGY | " | 256x15mer |
| " | 270-NYYWIL | " | 48x17mer |
| " | 393-FGVHY | " | 128x15mer |
| " | 423-FQGFFV | " | 64x17mer |
| " | 438-CNGEVQ | " | 128x17mer |
| Acetylcholine (muscarinic) GPCR | 111-VNNYFL | 23Total 5Human | 128x17mer |
| " | 130-MNL(FY)T | " | 64x14mer |
| " | 150-CDLWL | " | 128x14mer |
| " | 162-NASVMN | " | 256x17mer |
| " | 209-WAPAI | " | 192x15mer |
| " | 241-TFGTA | " | 256x14mer |
| " | 448-W(TA)PYN | " | 128x15mer |
| Histamine GPCR | 125-TASI(FL) | 10Total 2Human | 768x14mer |
| " | 439-M(AG)AFI | " | 192x15mer |
| " | 445-CW(IF)PYF | " | 192x18mer |
| Angiotensin GPCR | 40-IF(VI)(VI)G | 18Total 3Human | 384x14mer |
| " | 201-KN(IL)(LV)G | " | 576x14mer |

*FIG._1A*

| Gene Family | Motif (#-aa) | Members | Degeneracy |
|---|---|---|---|
| α2-Adrenergic GPCR | 66-APQNLF | 17Total 4Human | 512x17mer |
| " | 78-ADILV | " | 768x14mer |
| " | 109-YLALD | " | 512x14mer |
| " | 204-FFAPC | " | 128x15mer |
| " | 372-FTFVLA | " | 512x17mer |
| " | 386-CWFPFFF | " | 128x21mer |
| β-Adrenergic GPCR | 139-DVLCVT | 22Total 3Human | 512x17mer |
| " | 338-FTLCWL | " | 256x17mer |
| " | 377-(AG)FNP(LI) | " | 384x14mer |
| Rad51 | 114-GKTQ(FILV) | 60Total 6Human | 256x14mer |
| " | 160-(ILM)(FY)ID(TS) | " | 1152x14mer |
| bZIP (ATF1,CREA,CREB,CREM) | 222-KNREAA | 13Total 3Human | 256x17mer |
| bZIP (AP1,BAC1,JUNB,JUND) | 269-CRKRK | 21Total 4Human | 512x15mer |
| MSH2 & 3 | 355-W(IV)(KT)QP | 5Total 2Human | 512x15mer |
| MSH2, 3, & 6 | 669-GPNMGG | 8Total 3Human | 128x17mer |
| " | 761-DELGR | " | 256x14mer |
| MutL | 92-GFRGEA | 12Total 3Human | 512x17mer |
| TGF-β (BMP3, BM3B) | 385-FADIGW | 5Total 2Human | 192x18mer |
| TGF-β (BMP5-8) | 356-HELYV | 10Total 4Human | 256x15mer |
| TGF-β (BMP2 & 4) | 309-GWNDWIV | 13Total 2Human | 48x20mer |
| TGF1, 2, & 3 | 307-DLGWKW | 20Total 3Human | 128x18mer |
| XPG | 859-GSDDY(TC) | 12Total 2Human | 1024x14mer |

*FIG._1B*

| Amino Acid Seq. | Nucleic Acid Seq. |
|---|---|
| EAM(LF)(YFH) | GARGCNATGYTNY(AT) |
| FNEAK | TTYAAYGARGCNAAR |
| FTMYTT | TTYACNATGTAYACNAC |
| CYNFWM | TGYTAYAAYTTYTGGATG |
| YDFNHK | TAYGAYTTYAAYCAYAAR |
| VNNYFL | GTNAAYAAYTAYTTYYT |
| (ILM)(FY)ID(TS) | (ATC)TNT(TA)YAT(ATC)GAY(AT)(CG) |
| CW(IF)PYF | TGYTGG(AT)T(ATC)CCNTAYTTY |
| | N=GATC |
| | R=GA |
| | Y=CT |

*FIG._1C*

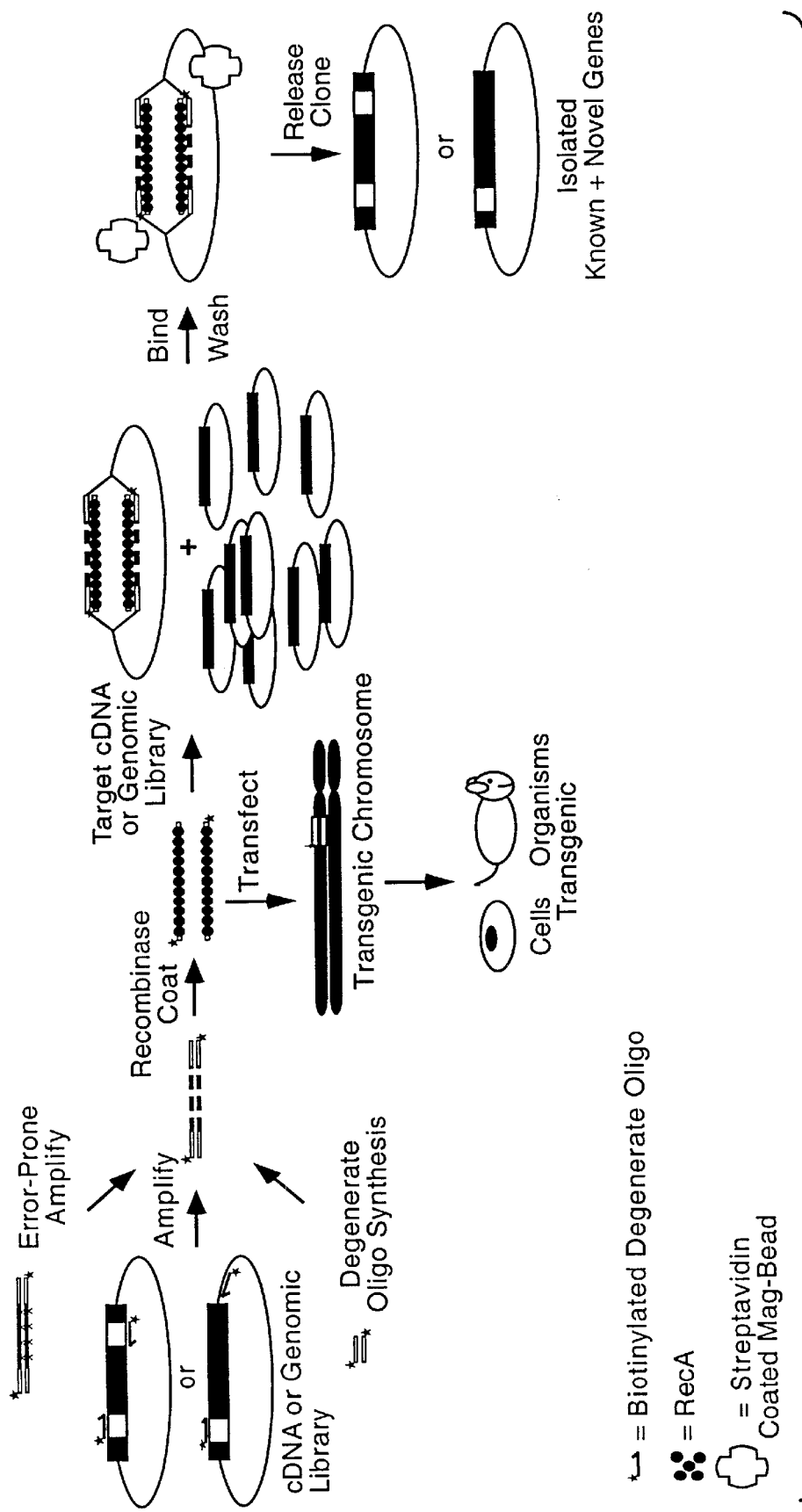
FIG._2

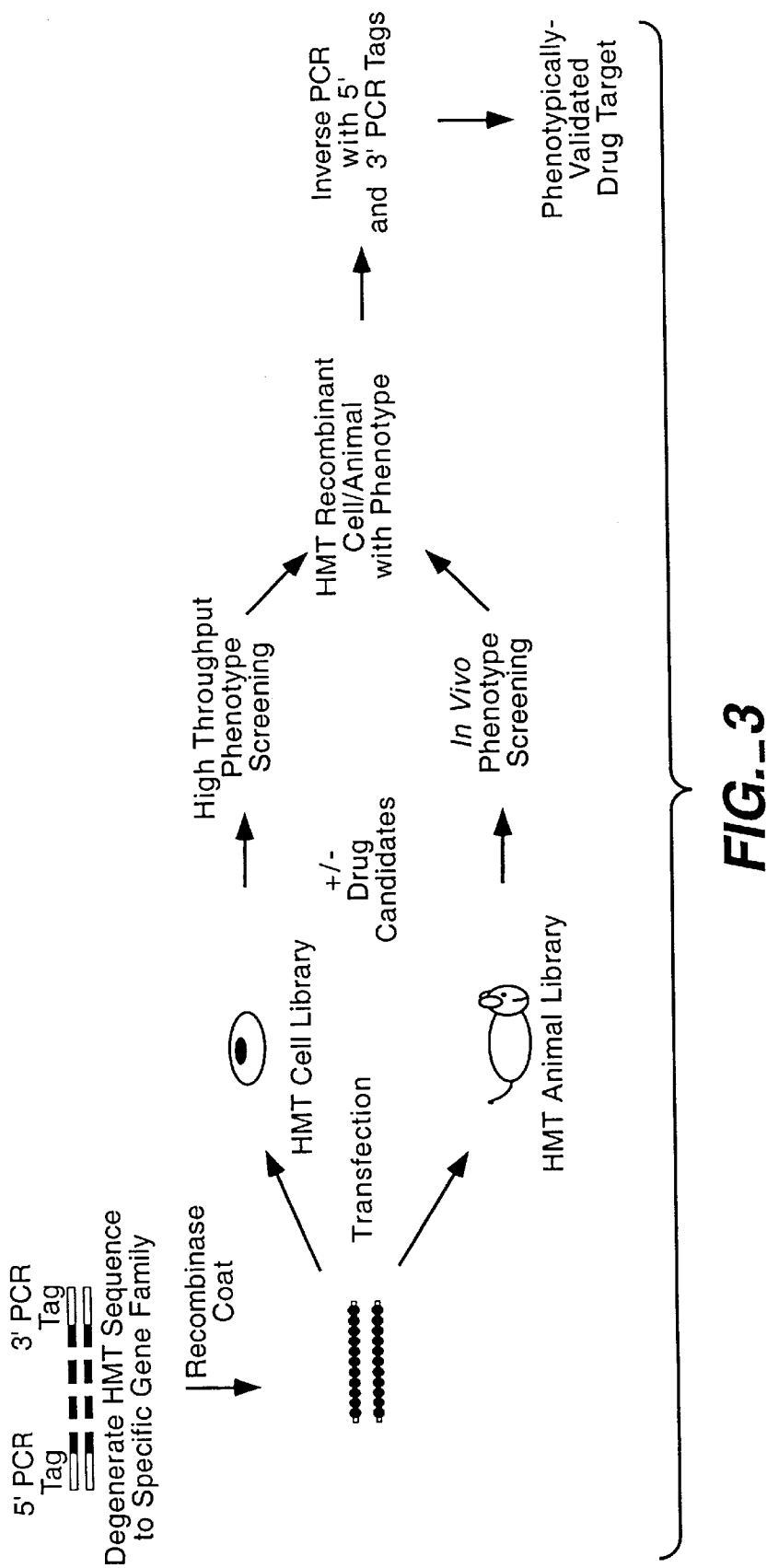
FIG._3

Human 14-3-3 isoforms

| | | | |
|---|---|---|---|
| Eta | 171 | IRLGLALNFSVFYYEIQNAPEQACLLAKQAFDDAIAELDTLNE | 213 |
| Beta | 168 | IRLGLALNFSVFYYEILNSPEKACSLAKTAFDEAIAELDTLNE | 209 |
| Theta | 166 | IRLGLALNFSVFYYEILNNPELACTLAKTAFDEAIAELDTLNE | 207 |
| Epsilo | 169 | IRLGLALNFSVFYYEILNSPDRACRLAKAAFDDAIAELDTLSE | 210 |
| Sigma | 168 | IRLGLALNFSVFHYEIANSPEEAISLAKTTFDEAMADLHTLSE | 209 |
| Zeta | 166 | IRLGLALNFSVFYYEILNSPDRACRLAKAAFDDAIAELDTLSE | 208 |

Rattus 14-3-3 isoforms

| | | | |
|---|---|---|---|
| Eta | 171 | IRLGLALNFSVFYYEIQNAPEQACLLAKQAFDDAIAELDTLNE | 213 |
| Beta | 168 | IRLGLALNFSVFYYEILNSPEKACSLAKTAFDEAIAELDTLNE | 209 |
| Theta | 166 | IRLGLALNFSVFYYEILNNPELACTLAKTAFDEAIAELDTLNE | 207 |
| Gamma | 171 | IRLGLALNYSVFYYEIQNAPEQACHLAKTAFDDAIAELDTLNE | 213 |
| Zeta | 166 | IRLGLALNFSVFYYEILNSPEKACSLAKTAFDEAIAELDTLSE | 207 |

Bovine 14-3-3 isoforms:

| | | | |
|---|---|---|---|
| Eta | 171 | IRLGLALNFSVFYYEIQNAPEQACLLAKQAFDDAIAELDTLNE | 213 |
| Beta | 166 | IRLGLALNFSVFYYEILNSPEKACSLAKTAFDEAIAELDTLNE | 208 |
| Gamma | 171 | IRLGLALNYSVFYYEIQNAPEQACHLAKTAFDDAIAELDTLNE | 213 |
| Epsilo | 169 | IRLGLALNFSVFYYEILNSPDRACRLAKAAFDDAIAELDTLSE | 211 |
| Zeta | 166 | IRLGLALNFSVFYYEILNAPEKACSLAKQAFDEAIAELDTLSE | 208 |

FIG._4

```
zeta    atcagactgg gtctggccct taacttctct gtgttctatt atgagattct
sigma   atccgcctgg gcctggccct gaactttcc  gtcttccact acgagatcgc
eta     atccggctgg gcctggccct caacttctcc gtgttctact atgagatcca
beta    attcgtcttg gtctggcact aaatttctca gtcttttact atgagattct
epsilo  attcgcttag gtcttgctct caattttcc  gtattctact acgaaattct
theta   atccgcctgg ggcttgctct taactttct  gtattttact atgagattct zeta    gaactcccca gagaaagcct gctctcttgc aaagacagct tttgatgaag
sigma   caacagcccc gaggaggcca tctctctggc caagaccact ttcgacgagg
eta     gaatgcacct gagcaagcct gcctcttagc caaacaagcc ttcgatgatg
beta    aaactctcct gaaaaggcct gtagcctggc aaaaacggca tttgatgaag
epsilo  taattcccct gaccgtgcct gcaggttggc aaaagcagct tttgatgatg
theta   taataaccca gagcttgcct gcacgctggc taaaacggct tttgatgagg zeta    ccattgctga acttgataca ttaagtgaa
sigma   ccatggctga tctgcacacc ctcagcgag
eta     ccatagctga gctggacaca ctaaacgag
beta    caattgctga attggatacg ctgaatgaa
epsilo  caattgcaga actggatacg ctgagtgaa
theta   ccattgctga acttgataca ctgaatgaa
```

FIG._5

Amino acids:
    (R)                    (K)
IELGLALNFSVFYYEIQNAPEQACLLAEQAFDDAIAELDTLNE

USE OF CONSENSUS SEQUENCES FOR TARGETED HOMOLOGOUS GENE ISOLATION AND RECOMBINATION IN GENE FAMILIES

This is a continuing application of U.S. application Ser. No. 60/070,734, filed Dec. 11, 1997.

FIELD OF THE INVENTION

The invention relates to compositions and methods for targeting sequence modifications in one or more genes of a related family of genes using enhanced homologous recombination techniques. The invention also relates to compositions and methods for isolating and identifying novel members of homologous sequences families. These techniques may be used to create animal or plant models of disease as well as to identify new targets for drug or pathogen screening.

BACKGROUND

Homologous recombination (or general recombination) is defined as the exchange of homologous segments anywhere along a length of two DNA molecules. An essential feature of general recombination is that the enzymes responsible for the recombination event can presumably use any pair of homologous sequences as substrates, although some types of sequence may be favored over others. Both genetic and cytological studies have indicated that such a crossing-over process occurs between pairs of homologous chromosomes during meiosis in higher organisms.

Alternatively, in site-specific recombination, exchange occurs at a specific site, as in the integration of phage λ into the E. coli chromosome and the excision of λ DNA from it. Site-specific recombination involves specific inverted repeat sequences; e.g. the Cre-loxP and FLP-FRT systems. Within these sequences there is only a short stretch of homology necessary for the recombination event, but not sufficient for it. The enzymes involved in this event generally cannot recombine other pairs of homologous (or nonhomologous) sequences, but act specifically.

Although both site-specific recombination and homologous recombination are useful mechanisms for genetic engineering of DNA sequences, targeted homologous recombination provides a basis for targeting and altering essentially any desired sequence in a duplex DNA molecule, such as targeting a DNA sequence in a chromosome for replacement by another sequence. Site-specific recombination has been proposed as one method to integrate transfected DNA at chromosomal locations having specific recognition sites (O'Gorman et al. (1991) Science 251: 1351; Onouchi et al. (1991) Nucleic Acids Res. 19: 6373). Unfortunately, since this approach requires the presence of specific target sequences and recombinases, its utility for targeting recombination events at any particular chromosomal location is severely limited in comparison to targeted general recombination.

Homologous recombination has also been used to create transgenic plants and animals. Transgenic organisms contain stably integrated copies of genes or gene constructs derived from another species in the chromosome of the transgenic organism. In addition, gene targeted animals can be generated by introducing cloned DNA constructs of the foreign genes into totipotent cells by a variety of methods, including homologous recombination. For example, animals that develop from genetically altered totipotent cells can contain the foreign gene in all somatic cells and also in germ-line cells. Currently methods for producing transgenic and targeted animals have been performed on totipotent embryonic stem cells (ES) and with fertilized zygotes. ES cells have an advantage in that large numbers of cells can be manipulated easily by homologous recombination in vitro before they are used to generate targeted animals. Currently, however, only embryonic stem cells from mice have been shown to contribute to the germ line. Alternatively, DNA can also be introduced into fertilized oocytes by micro-injection into pronuclei which are then transferred into the uterus of a pseudo-pregnant recipient animal to develop to term. The ability of mammalian and human cells to incorporate exogenous genetic material into genes residing on chromosomes has demonstrated that these cells have the general enzymatic machinery for carrying out homologous recombination required between resident and introduced sequences. These targeted recombination events can be used to correct mutations at known sites, replace genes or gene segments with defective ones, or introduce foreign genes into cells.

Traditionally, exogenous sequences transferred into eukaryotic cells undergo homologous recombination with homologous endogenous sequences only at very low frequencies, and are so inefficiently recombined that large numbers of cells must be transfected, selected, and screened in order to generate a desired correctly targeted homologous recombinant (Kucherlapati et al. (1984) Proc. Natl. Acad. Sci. (U.S.A.) 81: 3153; Smithies, 0. (1985) Nature 317: 230; Song et al. (1987) Proc. Natl. Acad. Sci. (U.S.A.) 84: 6820; Doetschman et al. (1987) Nature 330: 576; Kim and Smithies (1988) Nucleic Acids Res. 16: 8887; Doetschman et al. (1988) Proc. Natl. Acad. Sci. (USA) 85: 8583; Koller and Smithies (1989) Proc. Natl. Acad. Sci. (USA) 86: 8932; Shesely et al. (1991) Proc. Natl. Acad. Sci. (U.S.A.) 88: 4294; Kim et al. (1991) Gene 103: 227, which are incorporated herein by reference).

Several proteins or purified extracts having the property of promoting homologous recombination (i.e., recombinase activity) have been identified in prokaryotes and eukaryotes (Cox and Lehman (1987) Ann. Rev. Biochem. 56: 229; Radding, C. M. (1982) ANNU. Rev. Genet. 16:405; Madiraju et al. (1988) Proc. Natl. Acad. Sci. (U.S.A.) 85: 6592; McCarthy et al. (1988) Proc. Natl. Acad. Sci. (U.S.A.) 85: 5854; Lopez et al. (1987) Nucleic Acids Res. 15:5643,6813, which are incorporated herein by reference). These general recombinases presumably promote one or more steps in the formation of homologously-paired intermediates, strand-exchange, gene conversion, and/or other steps in the process of homologous recombination.

The frequency of homologous recombination in prokaryotes is significantly enhanced by the presence of recombinase activities. Several purified proteins catalyze homologous pairing and/or strand exchange in vitro, including: E. coli recA protein, the T4 uvsX protein, the rec1 protein from Ustilago maydis, and Rad51 protein from S. cerevisiae (Sung et al., Science 265:1241 (1994)) and human cells (Baumann et al., Cell 87:757 (1996)). Additional members of this protein family have been identified by homology and function including Rad51A, B, C, D & E. Dosanjh, et cl., (1998) Nucleic Acid Res. 26:1179–1184 and dmc1. Recombinases and dmel, like the recA protein of E. coli are proteins which promote strand pairing and exchange. The most studied recombinase to date has been the recA recombinase of E. coli, which is involved in homology search and strand exchange reactions (see, Cox and Lehman (1987) ANNU. Rev. Biochem. 56:229. RecA is required for induction of the SOS repair response, DNA repair, and efficient genetic recombination in E coli. RecA can catalyze homologous pairing of a linear duplex DNA and a homologous single strand DNA in vitro. In contrast to site-specific recombinases, proteins like recA which are involved in general recombination recognize and promote pairing of DNA structures on the basis of shared homology, as has been shown by several in vitro experiments (Hsieh and Camerini-Otero (1989) *J. Biol. Chem.* 264: 5089; Howard-Flanders et al. (1984) *Nature* 309: 215; Stasiak et al. (1984) *Cold Spring Harbor Symp. Quant. Biol.* 49: 561; Register et al. (1987) *J. Biol. Chem.* 262: 12812). Several investigators have used recA protein in vitro to promote homologously paired triplex DNA (Cheng et al. (1988) *J. Biol. Chem.* 263: 15110; Ferrin and Camerini-Otero (1991) *Science* 354: 1494; Ramdas et al. (1989) *J. Biol Chem.* 264: 11395; Strobel et al. (1991) *Science* 254: 1639; Hsieh et al. (1990) *Genes Dev.* 4:1951; Rigas et al. (1986) *Proc. Natl. Acad. Sci. (U.S.A.)* 83: 9591; and Camerini-Otero et al. U.S. Pat. No. 7,611,268, which are incorporated herein by reference).

Recent advances have resulted in techniques allowing enhanced homologous recombination (EHR) using recombinases such as recA and Rad51 and single-stranded nucleic acids that have sequence heterologies. This allows sequence modifications to be specifically targeted to virtually any genomic position. See for example, PCT US93/03868 and PCT US98/05223, both of which are expressly incorporated herein by reference.

One area of pressing interest in biology is within the area of "functional genomics", i.e. the correlation of genotype and phenotype. This requires animal systems, since phenotypic changes must be evaluated in vivo. Similarly, and related to this idea, is the elucidation and characterization of gene families, i.e. genes or proteins that are structurally related, i.e. they have sequence homologies between the members of the family. Since presumably many, if not most, disease states are caused by multiple gene interactions, the ability to evaluate interactions among genes, and particularly within or between gene families, at the phenotype level, would be extremely valuable.

The functional genomics tools that allow facile identification and engineering of gene family members in animals and cells, however, are not yet available. While the amino acid sequence motifs shared between gene family members may be identical, due to degeneracy in the DNA code, the DNA sequence identity may be significantly less. Hence, one criterion necessary for genetic modifications of gene family members is development of homologous recombination technologies that can be used to clone and modify similar DNA sequences that share little sequence identity. This is particularly important since homologous recombination in cells normally requires significant sequence identity to work efficiently. Relaxing the amount of sequence identity needed for homologous recombination allows greater flexibility to target related genes for creating transgenic animals and cells containing modifications in gene family consensus sequences, and also will allow the rapid cloning, generation of gene family specific libraries, and evolution of gene family members.

Accordingly, it is an object of the present invention to provide compositions and methods for the evaluation and characterization of gene families and the role of individual and sets of genes in disease states.

SUMMARY OF THE INVENTION

It is an object of the present invention to provide compositions comprising at least one recombinase and at least two single-stranded targeting polynucleotides which are substantially complementary to each other and each having a consensus homology clamp for a gene family.

In an additional aspect, the invention provides compositions comprising at least one recombinase and a plurality of pairs of single stranded targeting polynucleotides, where the plurality of pairs comprises a set of degenerate probes encoding the consensus sequence.

In a further aspect, the invention provides kits comprising the compositions of the invention and at least one reagent In an additional aspect, the invention provides methods for targeting a sequence modification in at least one member of a consensus family of genes in a cell by homologous recombination. The method comprises introducing into at least one cell at least one recombinase and at least two single-stranded targeting polynucleotides which are substantially complementary to each other and each having a consensus homology clamp for the family. The method can additionally comprise identifying a target cell having a targeted sequence modification.

In a further aspect, the invention provides methods of making a non-human organism with a targeted sequence modification in at least one member of a gene family. The method comprises introducing into a cell at least one recombinase and at least two single-stranded targeting polynucleotides which are substantially complementary to each other and each having a consensus homology clamp for said family. The cell is then subjected to conditions that result in the formation of an animal, and the animal has at least one modification in at least one member of a consensus family of genes.

In an additional aspect, the invention provides methods of isolating a member of a gene family comprising a protein consensus sequence. The method comprises adding to a complex mixture of nucleic acids at least one recombinase and at least two single-stranded targeting polynucleotides which are substantially complementary to each other and each having a consensus homology clamp for said family. At least one of the targeting polynucleotides comprises a purification tag. The method is done under conditions whereby the targeting polynucleotides form a complex with the member, and the family member is isolated using said purification tag. The complex nucleic acid mixture may be a cDNA library, a cell, RNA or a restriction endonucleases genomic digest.

In a further aspect, the invention provides non-human organisms containing a sequence modification in an endogenous consensus functional domain of a gene member of a gene family.

BRIEF DESCRIPTION OF THE DRAWINGS

FIGS. 1A and 1B (SEQ ID NOS:1–61) depict a table of protein families and consensus protein motifs. The gene family is a family or subfamily with common function or sequence homology used to determine consensus motifs. The motif is the amino acid consensus sequence common to the family members, and amino acid position is for the first human example. Parenthetical amino acids refers to all residues found at that single position within the family. Members refers to the homologous (total and human members) used to determine consensus sites. The degeneracy refers to the number and length of different oligonucleotides needed in one synthesis to code for all the consensus amino acids used. FIG. 1C (SEQ ID NOS:1, 5–6, 10, 21, 28, 37, 50 and 79–96) shows examples of DNA degeneracy.

FIG. 2 depicts a schematic for gene family member isolation and modification. The degenerate probe can be made by several different means including those shown. Libraries or linear nucleic acids can be used for targeting. Capture can utilize a biofin moiety as shown or others, described in the text and known in the art.

FIG. 3 depicts gene family member targeting in animals and cells.

FIG. 4 (SEQ ID NOS:62–77) depicts 14-3-3 protein binding sites in different species and isoforms.

FIG. 5 (SEQ ID NOS:87–92) depicts 14-3-3 the nucleic acid sequences encoding the human binding sites.

FIG. 6 (SEQ ID NO:78) depicts the protein consensus sequence for the modification of the 14-3-3 binding site.

DETAILED DESCRIPTION OF THE INVENTION

The present invention is directed to the use of homology motif tags (HMTs) in targeted homologous recombination to elucidate disease mechanisms and to identify disease targets contained within gene families related by the presence of one or more common domains. That is, there are a large number of gene families that contain genes related by the presence of similar functional domains, i.e. binding domains for substrates or other proteins, enzymatic domains such as kinase or protease domains, signaling and regulator domains, receptor binding domains, ATP binding domains, leucine zipper domains, zinc finger domains, etc. These functional domains frequently result in primary sequence homology; that is, related functional domains have related sequences. Many of these functional domains have been studied and so-called "consensus sequences" identified; that is, an average sequence derived from a number of related sequences. Each residue (or set of residues) of the consensus sequence is the most frequent at that position in the set under consideration. Consensus sequences can be either amino acid or nucleic acid consensus sequences, with amino acid sequences being used to generate nucleic acid consensus sequences.

Interestingly, while a wide variety of gene families are known, the majority of drug targets come from only four of these gene families. These are the G-protein coupled or seven-transmembrane domain receptors, nuclear (hormone) receptors, ion channels, esterases. Other important gene families are enzymes, including recombinases. Of the top 100 pharmaceutical drugs, 18 bind to seven-transmembrane receptors, 10 to nuclear receptors and 16 to ion channels.

By using HMTs directed to the consensus sequences of gene families for homologous recombination and particularly enhanced homologous recombination methods, sequence modifications may be made to any number of targeted genes in a related family.

The present invention can thus be used in a variety of important ways. First, HMTs can be used in the creation of transgenic animal and plant models of disease. Thus, for example, HMTs used in homologous recombination methods can generate animals that have a wide variety of mutations in a wide variety of related genes, potentially resulting in a wide variety of phenotypes, including phenotypes related to disease states. This may also be done on a cellular level, to identify genes involved in cellular phenotypes, i.e. target identification. Secondly, HMT targeting can be used in cells or animals that are diseased or altered; in essence, HMT targeting can be done to identify "reversion" genes, genes that can modulate disease states caused by different genes, either genes within the same gene family or a completely different gene family. Thus, for example the loss of one type of enzymatic activity, resulting in a disease phenotype, may be compensated by alterations in a different but homologous enzymatic activity. For example, the effects of the elimination of one kinase in a MAP kinase cascade can be overcome by another parallel pathway.

Accordingly, the present invention provides methods and compositions utilizing homology motif tags (HMTs) or consensus sequences. By "homology motif tag" or "protein consensus sequence" herein is meant an amino acid consensus sequence of a gene family. By "consensus nucleic acid sequence" herein is meant a nucleic acid that encodes a consensus protein sequence of a functional domain of a gene family. In addition, "consensus nucleic acid sequence" can also refer to cis sequences that are non-coding but can serve a regulatory or other role. As outlined below, generally a library of consensus nucleic acid sequences are used, that comprises a set of degenerate nucleic acids encoding the protein consensus sequence. A wide variety of protein consensus sequences for a number of gene families are known. A "gene family" therefore is a set of genes that encode proteins that contain a functional domain for which a consensus sequence can be identified. However, in some instances, a gene family includes non-coding sequences; for example, consensus regulatory regions can be identified. For example, gene family/consensus sequences pairs are known for the G-protein coupled receptor family, the AAA-protein family, the bZIP transcription factor family, the mutS family, the recA family, the Rad51 family, the dmel family, the recF family, the SH2 domain family, the Bcl-2 family, the single-stranded binding protein family, the TFIID transcription family, the TGF-beta family, the TNF family, the XPA family, the XPG family, actin binding proteins, bromo-domain GDP exchange factors, MCM family, ser/thr phosphatase family, etc.

As will be appreciated by those in the art, the proteins of the gene families generally do not contain the exact consensus sequences; generally consensus sequences are artificial sequences that represent the best comparison of a variety of sequences. The actual sequence that corresponds to the functional sequence within a particular protein is termed a "consensus functional domain" herein; that is, a consensus functional domain is the actual sequence within a protein that corresponds to the consensus sequence. A consensus functional domain may also be a "predetermined endogenous DNA sequence" (also referred to herein as a "predetermined target sequence") that is a polynucleotide sequence contained in a target cell. Such sequences can include, for example, chromosomal sequences (e.g., structural genes, regulatory sequences including promoters and enhancers, recombinatorial hotspots, repeat sequences, integrated proviral sequences, hairpins, palindromes), episomal or extrachromosomal sequences (e.g., replicable plasmids or viral replication intermediates) including chloroplast and mitochondrial DNA sequences. By "predetermined" or "pre-selected" it is meant that the consensus functional domain target sequence may be selected at the discretion of the practitioner on the basis of known or predicted sequence information, and is not constrained to specific sites recognized by certain site-specific recombinases (e.g., FLP recombinase or CRE recombinase).

In some embodiments, the predetermined endogenous DNA target sequence will be other than a naturally occurring germline DNA sequence (e.g., a transgene, parasitic, mycoplasmal or viral sequence).

In a preferred embodiment, the gene family is the G-protein coupled receptor family, which has over 900 identified members, including several subfamilies. In a preferred embodiment, the G-protein coupled receptors are from subfamily 1 and are also called R7G proteins. They are an extensive group of receptors which recognize hormones, neurotransmitters, odorants and light and transduce extracellular signals by interaction with guanine (G) nucleotide-binding proteins. The structure of all these receptors is thought to be virtually identical, and they contain seven hydrophobic regions, each of which putatively spans the membrane. The N-terminus is extracellular and is frequently glycosylated, and the C-terminus is cytoplasmic and generally phosphorylated. Three extracellular loops alternate with three cytoplasmic loops to link the seven transmembrane regions. G-protein coupled receptors include, but are not limited to: the class A rhodopsin first subfamily, including amine (acetylcholine (muscarinic), adrenoceptors, domamine, histamine, serotonin, octopamine), peptides (angiotensin, bombesin, bradykinin, C5a anaphylatoxin, Fmet-leu-phe, interleukin-8, chemokine, CCK, endothelin, mealnocortin, neuropeptide Y, neurotensin, opioid, somatostatin, tachykinin, thrombin, vasopressin-like, galanin, proteinase activated), hormone proteins (follicle stimulating hormone, lutropin-choriogonadotropic hormone, thyrotropin), rhodopsin (vertebrate), olfactory (olfactory type 1-11, gustatory), prostanoid (prostaglandin, prostacyclin, thromboxane), nucleotide (adenosine, purinoceptors), cannabis, platelet activating factor, gonadotropin-releasing hormone (gonadotropin releasing hormone, thyrotropin-releasing hormone, growth hormone secretagogue), melatonin, viral proteins, MHC receptor, Mas proto-oncogene, EBV-induced and glucocorticoid induced; the class B secretin second subfamily, including calcitonin, corticotropin releasing factor, gastric inhibitory peptide, glucagon, growth hormone releasing hormone, parathyroid hormone, secretin, vasoactive intestinal polypeptide, and diuretic hormone; the class C metabotropic glutamate third subfamily, including metabrotropic glutamate and extracellular calcium-sensing agents; and the class D pheromone fourth subfamily.

Because of the large number of family members, these large classes of GPCRs can be further subdivided into subfamilies. Examples of these subfamilies are included in FIGS. 1A&B (SEQ ID NOS:1–48) where metabotropic is from class C; calcitonin, glucagon, vasoactive and parathyroid are from class B; and acetylcholine, histamine angiotensin, α2- and β-adrenergic are from class A. From each subfamily small protein consensus sequences can be derived from sequence alignments. For example, FIG. 1A shows 6 motifs (SEQ ID NOS:1–6) for the metabotripic glutamate like GPRCs derived from the indicated number of family members. FIG. 1C shows certain examples like the first "EAM (LF) (YFH)" (SEQ ID NO:1) using the single letter amino acid code as is known in the art. Using the protein consensus sequence, degenerate nucleic acid probes are made to encode the protein consensus sequence, as is generally shown in FIG. 1, as is well known in the art. The protein sequence is encoded by DNA triplets which are deduced using standard tables. In some cases additional degeneracy is used to enable production in one oligonucleotide synthesis. In many cases motifs were chosen to minimize degeneracy. The examples shown in FIGS. 1A–C (SEQ ID NOS:1–61 and 79–86) were designed to facilitate use for amplification of neighboring sequences as shown in FIG. 2. This can utilize two motifs as indicated by faithful or error prone amplification. Alternatively outside sequences can be used as is indicated using vector sequence. In addition degenerate oligos can be synthesized and used directly in the procedure without amplification.

As diagramed in FIG. 2, these double stranded (ds) DNA probes are denatured and coated with RecA or another recombinase such as Rad51. This material can be used to bind to and allow capture of specific clones from cDNA or genomic libraries. Alternatively this material can be introduced into cells producing transgenic cells or animals with alterations in related family members.

In addition to the first subfamily of G-protein coupled receptors, there is a second subfamily encoding receptors that bind peptide hormones that do not show sequence similarity to the first R7G subfamily. All the characterized receptors in this subfamily are coupled to G-proteins that activate both adenylyl cyclase and the phosphatidylinositol-calcium pathway. However, they are structurally similar; like classical R7G proteins they putatively contain seven transmembrane regions, a glycosylated extracellular N-terminus and a cytoplasmic C-terminus. Known receptors in this subfamily are encoded on multiple exons, and several of these genes are alternatively spliced to yield functionally distinct products. The N-terminus contains five conserved cysteine residues putatively important in disulfide bonds. Known G-protein coupled receptors in this subfamily are listed above.

In addition to the first and second subfamilies of G-protein coupled receptors, there is a third subfamily encoding receptors that bind glutamate and calcium but do not show sequence similarity to either of the other subfamilies. Structurally, this subfamily has signal sequences, very large hydrophobic extracellular regions of about 540 to 600 amino acids that contain 17 conserved cysteines (putatively involved in disulfides), a region of about 250 residues that appear to contain seven transmembrane domains, and a C-terminal cytoplasmic domain of variable length (50 to 350 residues). Known G-protein coupled receptors of this subfamily are listed above.

In a preferred embodiment, the gene family is the bZIP transcription factor family. This eukaryotic gene family encodes DNA binding transcription factors that contain a basic region that mediates sequence specific DNA binding, and a leucine zipper, required for dimerization. The bZIP family includes, but is not limited to, AP-1, ATF, CREB, CREM, FOS, FRA, GBF, GCN4, HBP, JUN, MET4, OCS1, OP, TAF1, XBP1, and YBBO.

In a preferred embodiment, the gene family is involved in DNA mismatch repair, such as mutL, hexB and PMS1. Members of this family include, but are not limited to, MLH1, PMS1, PMS2, HexB and MutL. The protein consensus sequence is G-F-R-G-E-A-L (SEQ ID NO:95).

In a preferred embodiment, the gene family is the mutS family, also involved in mismatch repair of DNA, directed to the correction of mismatched base pairs that have been missed by the proofreading element of the DNA polymerase complex. MutS gene family members include, but are not limited to, MSH2, MSH3, MSH6 and MutS.

In a preferred embodiment, the gene family is the recA family. The bacterial recA is essential for homologous recombination and recombinatorial repair of DNA damage. RecA has many activities, including the formation of nucleoprotein filaments, binding to single stranded and double stranded DNA, binding and hydrolyzing ATP, recombinase activity and interaction with lexA causing lexA activation and autocatalytic cleavage. RecA family members include those from *E. coli*, drosophila, human, lily, etc. specifically including but not limited to, *E. coli* recA, Rec1, Rec2, Rad51, Rad51B, Rad51C, Rad51D, Rad51E, XRCC2 and DMC1.

In a preferred embodiment, the gene family is the recF family. The prokaryotic recF protein is a single-stranded DNA binding protein which also putatively binds ATP. RecF is involved in DNA metabolism; it is required for recombinatorial DNA repair and for induction of the SOS response. RecF is a protein of about 350 to 370 amino acid residues; there is a conserved ATP-binding site motif 'A' in the N-terminal section of the protein as well as two other conserved regions, one located in the central section and the other in the C-terminal section.

In a preferred embodiment, the gene family is the Bcl-2 family. Programmed cell death (PCD), or apoptosis, is induced by events such as growth factor withdrawal and toxins. It is generally controlled by regulators, which have either an inhibitory effect (i.e. anti-apoptotic) or block the protective effect of inhibitors (pro-apoptotic). Many viruses have found a way of countering defensive apoptosis by encoding their own anti-apoptotic genes thereby preventing their target cells from dying too soon.

All proteins belonging to the Bcl-2 family contain at least one of a BH1, BH2, BH3 or BH4 domain. All anti-apoptotic proteins contain BH1 and BH2 domains, some of them contain an additional N-terminal BH4 domain (such as Bcl-2, Bcl-x(L), Bcl-W, etc.), which is generally not found in pro-apoptotic proteins (with the exception of Bcl-x(S). Generally all pro-apoptotic proteins contain a BH3 domain (except for Bad), thought to be crucial for the dimerization of the proteins with other Bcl-2 family members and crucial for their killing activity. In addition, some of the pro-apoptotic proteins contain BH1 and BH2 domains (such as Bax and Bak). The BH3 domain is also present in some anti-apoptosis proteins, such as Bcl-2 and Bcl-x(L). Known Bcl-2 proteins include, but are not limited to, Bcl-2, Bcl-x(L), Bcl-W, Bcl-x(S), Bad, Bax, and Bak.

In a preferred embodiment, the gene family is the site-specific recombinase family. Site-specific recombination plays an important role in DNA rearrangement in prokaryotic organisms. Two types of site-specific recombination are known to occur: a) recombination between inverted repeats resulting in the reversal of a DNA segment; and b) recombination between repeat sequences on two DNA molecules resulting in their cointegration, or between repeats on one DNA molecule resulting the excision of a DNA fragment. Site-specific recombination is characterized by a strand exchange mechanism that requires no DNA synthesis or high energy cofactor; the phosphodiester bond energy is conserved in a phospho-protein linkage during strand cleavage and re-ligation.

Two unrelated families of recombinases are currently known. The first, called the "phage integrase" family, groups a number of bacterial, phage and yeast plasmid enzymes. The second, called the "resolvase" family, groups enzymes which share the following structural characteristics: an N-terminal catalytic and dimerization domain that contains a conserved serine residue involved in the transient covalent attachment to DNA, and a C-terminal helix-turn-helix DNA-binding domain.

In a preferred embodiment, the gene family is the single-stranded binding protein family. The *E. coli* single-stranded binding protein (ssb), also known as the helix-destabilizing protein, is a protein of 177 amino acids. It binds tightly as a homotetramer to a single-stranded DNA ss-DNA) and plays an important role in DNA replication, recombination and repair. Members of the ssb family include, but are not limited to, *E. coli* ssb and eukaryotic RPA proteins.

In a preferred embodiment, the gene family is the TFIID transcription family. Transcription factor TFIID (or TATA-binding protein, TBP), is a general factor that plays a major role in the activation of eukaryotic genes transcribed by RNA polymerase II. TFIID binds specifically to the TATA box promoter element which lies close to the position of transcription initiation. There is a remarkable degree of sequence conservation of a C-terminal domain of about 180 residues in TFIID from various eukaryotic sources. This region is necessary and sufficient for TATA box binding. The most significant structural feature of this domain is the presence of two conserved repeats of a 77 amino-acid region.

In a preferred embodiment, the gene family is the TGF-β family. Transforming growth factor-β (TGF-β) is a multi-functional protein that controls proliferation, differentiation and other functions in many cell types. TGF-β-1 is a protein of 112 amino acid residues derived by proteolytic cleavage from the C-terminal portion of the precursor protein. Members of the TGF-β family include, but are not limited to, the TGF-1–3 subfamily (including TGF1, TGF2, and TGF3); the BMP3 subfamily (BM3B, BMP3); the BMP5–8 subfamily (BM8A, BMP5, BMP6, BMP7, and BMP8); and the BMP 2 & 4 subfamily (BMP2, BMP4, DECA).

Some protein consensus sequences of the TGF-β family are shown in FIG. 1A (SEQ ID NOS:57–59).

In a preferred embodiment, the gene family is the TNF family. A number of cytokines can be grouped into a family on the basis of amino acid sequence, as well as structural and functional similarities. These include (1) tumor necrosis factor (TNF), also known as cachectin or TNF-a, which is a cytokine with a wide variety of functions. TNF-α can cause cytolysis of certain tumor cell lines; it is involved in the induction of cachexia; it is a potent pyrogen, causing fever by direct action or by stimulation of interleukin-1 secretion; and it can stimulate cell proliferation and induce cell differentiation under certain conditions; (2) lymphotoxin-α (LT-α) and lymphotoxin-β(LT-β), two related cytokines produced by lymphocytes and which are cytotoxic for a wide range of tumor cells in vitro and in vivo; (3) T cell antigen gp39 (CD40L), a cytokine that seems to be important in B-cell development and activation; (4) CD27L, a cytokine that plays a role in T-cell activation; it induces the proliferation of costimulated T cells and enhances the generation of cytolytic T cells; (5) CD30L, a cytokine that induces proliferation of T-cells; (6) FASL, a cytokine involved in cell death; (8) 4-1 BBL, an inducible T cell surface molecule that contributes to T-cell stimulation; (9) OX40L, a cytokine that co-stimulates T cell proliferation and cytokine production; and (10), TNF-related apoptosis inducing ligand (TRAIL), a cytokine that induces apoptosis.

In a preferred embodiment, the gene family is the XPA family. Xeroderma pigmentosa (XP) is a human autosomal recessive disease, characterized by a high incidence of sunlight-induced skin cancer. Skin cells associated with this condition are hypersensitive to ultaviolet light, due to defects in the incision step of DNA excision repair. There are a minimum of 7 genetic complementation groups involved in this disorder: XPA to XPG. XPA is the most common form of the disease and is due to defects in a 30 kD nuclear protein called XPA or (XPAC). The sequence of XPA is conserved from higher eukaryotes to yeast (gene RAD14). XPA is a hydrophilic protein of 247 to 296 amino acid residues that has a C4-type zinc finger motif in its central section.

In a preferred embodiment, the gene family is the XPG family. The defect in XPG can be corrected by a 133 kD nuclear protein called XPG (or XPGC). Members of the XPG family include, but are not limited to, FEN1, XPG, RAD2, EXO1, and DIN7.

Once having identified a gene family and a consensus sequence, the compositions of the invention can be made. The compositions of the invention comprise at least one recombinase and at least two single-stranded targeting polynucleotides which are substantially complementary to each other and each have a consensus homology clamp for a gene family.

By "recombinase" herein is meant a protein that, when included with an exogenous targeting polynucleotide, provide a measurable increase in the recombination frequency and/or localization frequency between the targeting polynucleotide and an endogenous predetermined DNA sequence.

Thus, in a preferred embodiment, increases in recombination frequency from the normal range of $10^{-8}$ to $10^{31\ 4}$, to $10^{-4}$ to $10^1$, preferably $10^{-3}$ to $101^1$, and most preferably $10^{-2}$ to $10^0$, may be achieved.

In the present invention, recombinase refers to a family of RecA-like recombination proteins all having essentially all or most of the same functions, particularly: (i) the recombinase protein's ability to properly bind to and position targeting polynucleotides on their homologous targets and (ii) the ability of recombinase protein/targeting polynucleotide complexes to efficiently find and bind to complementary endogenous sequences. The best characterized recA protein is from E. coli, in addition to the wild-type protein a number of mutant recA proteins have been identified (e.g., recA803; see Madiraju et al., PNAS USA 85(18):6592 (1988); Madiraju et al, Biochem. 31:10529 (1992); Lavery et al., J. Biol. Chem. 267:20648 (1992)). Further, many organisms have recA-like recombinases with strand-transfer activities (e.g., Fugisawa et al., (1985) Nucl. Acids Res. 13: 7473; Hsieh et al., (1986) Cell 44: 885; Hsieh et al., (1989) J. Biol. Chem. 264: 5089; Fishel et al., (1988) Proc. Natl. Acad. Sci. (USA) 85: 3683; Cassuto et al., (1987) Mol. Gen. Genet. 208: 10; Ganea et al., (1987) Mol. Cell Biol. 7: 3124; Moore et al., (1990) J. Biol. Chem. 19: 11108; Keene et al., (1984) Nucl. Acids Res. 12: 3057; Kimeic, (1984) Cold Spring Harbor Svmp. 48: 675; Kmeic, (1986) Cell 44: 545; Kolodner et al., (1987) Proc. Natl. Acad. Sci. USA 84: 5560; Sugino et al., (1985) Proc. Natl. Acad. Sci. USA 85: 3683; Halbrook et al., (1989) J. Biol. Chem. 264: 21403; Eisen et al., (1988) Proc. Natl. Acad. Sci. USA 85: 7481; McCarthy et al., (1988) Proc. Natl. Acad. Sci. USA 85: 5854; Lowenhauptet al., (1989) J. Biol. Chem. 264: 20568, which are incorporated herein by reference. Examples of such recombinase proteins include, for example but not limited to: recA, recA803, uvsX, and other recA mutants and recA-like recombinases (Roca, A. I. (1990) Crit. Rev. Biochem. Molec. Biol. 25: 415), sep1 (Kolodner et al. (1987) Proc. Natl. Acad. Sci. (U.S.A.) 84:5560; Tishkoff et al. Molec. Cell. Biol. 11:2593), RuvC (Dunderdale et al. (1991) Nature 354: 506), DST2, KEM1, XRN1 (Dykstra et al. (1991) Molec. Cell. Biol. 11:2583), STPα/DST1 (Clark et al. (1991) Molec. Cell. Biol.11:2576), HPP-1 (Moore et al. (1991) Proc. Natl. Acad. Sci. (U.S.A.) 88:9067), other target recombinases (Bishop et al. (1992) Cell 69: 439; Shinohara et al. (1992) Cell 69: 457); incorporated herein by reference. RecA may be purified from E. coli strains, such as E. coli strains JC12772 and JC15369 (available from A. J. Clark and M. Madiraju, University of California-Berkeley, or purchased commercially). These strains contain the recA coding sequences on a "runaway" replicating plasmid vector present at a high copy numbers per cell. The recA803 protein is a high-activity mutant of wild-type recA. The art teaches several examples of recombinase proteins, for example, from Drosophila, yeast, plant, human, and non-human mammalian cells, including proteins with biological properties similar to recA (i.e., recA-like recombinases), such as Rad51, Rad57, dmel from mammals and yeast, and Pk-rec (see Rashid et al., Nucleic Acid Res. 25(4):719 (1997), hereby incorporated by reference). In addition, the recombinase may actually be a complex of proteins, i.e. a "recombinosome". In addition, included within the definition of a recombinase are portions or fragments of recombinases which retain recombinase biological activity, as well as variants or mutants of wild-type recombinases which retain biological activity, such as the E. coli recA803 mutant with enhanced recombinase activity.

In a preferred embodiment, recA or rad51 is used. For example, recA protein is typically obtained from bacterial strains that overproduce the protein: wild-type E. coli recA protein and mutant recA803 protein may be purified from such strains. Alternatively, recA protein can also be purchased from, for example, Pharmacia (Piscataway, N.J.) or Boehringer Mannheim (Indianapolis, Ind.).

RecA proteins, and its homologs, form a nucleoprotein filament when it coats a single-stranded DNA. In this nucleoprotein filament, one monomer of recA protein is bound to about 3 nucleotides. This property of recA to coat single-stranded DNA is essentially sequence independent, although particular sequences favor initial loading of recA onto a polynucleotide (e.g., nucleation sequences). The nucleoprotein filament(s) can be formed on essentially any DNA molecule and can be formed in cells (e.g., mammalian cells), forming complexes with both single-stranded and double-stranded DNA, although the loading conditions for dsDNA are somewhat different than for ssDNA.

The recombinase is combined with targeting polynucleotides as is more fully outlined below. By "nucleic acid" or "oligonucleotide" or "polynucleotide" or grammatical equivalents herein means at least two nucleotides covalently linked together. A nucleic acid of the present invention will generally contain phosphodiester bonds, although in some cases nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate, phosphorodithioate, O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). These modifications of the ribose-phosphate backbone or bases may be done to facilitate the addition of other moieties such as chemical constituents, including 2' O-methyl and 5' modified substituents, as discussed below, or to increase the stability and half-life of such molecules in physiological environments.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo-and ribo-nucleotides, and any combination of bases, including uracil, adenine, thymine, cytosine, guanine, inosine, xathanine and hypoxathanine, etc. Thus, for example, chimeric DNA-RNA molecules may be used such as described in Cole-Strauss et al., Science 273:1386 (1996) and Yoon et al., PNAS USA 93:2071 (1996), both of which are hereby incorporated by reference.

In general, the targeting polynucleotides may comprise any number of structures, as long as the changes do not substantially effect the functional ability of the targeting polynucleotide to result in homologous recombination. For example, recombinase coating of alternate structures should still be able to occur.

By "targeting polynucleotides" herein is meant the polynucleotides used to make alterations in the consensus functional domains of members of gene families as described herein. Targeting polynucleotides are generally ssDNA or dsDNA, most preferably two complementary single-stranded DNAs.

Targeting polynucleotides are generally at least about 5 to 2000 nucleotides long, preferably about 12 to 200 nucleotides long, at least about 200 to 500 nucleotides long, more preferably at least about 500 to 2000 nucleotides long, or longer; however, as the length of a targeting polynucleotide increases beyond about 20,000 to 50,000 to 400,000 nucleotides, the efficiency or transferring an intact targeting polynucleotide into the cell decreases. The length of homology may be selected at the discretion of the practitioner on the basis of the sequence composition and complexity of the predetermined endogenous target DNA sequence(s) and guidance provided in the art, which generally indicates that 1.3 to 6.8 kilobase segments of homology are preferred when non-recombinase mediated methods are utilized (Hasty et al. (1991) *Molec. Cell. Biol.* 11: 5586; Shulman et al. (1990) *Molec. Cell. Biol.* 10: 4466, which are incorporated herein by reference).

Targeting polynucleotides have at least one sequence that substantially corresponds to, or is substantially complementary to, a consensus functional domain, i.e. the predetermined endogenous DNA sequence (i.e., a DNA sequence of a polynucleotide located in a target cell, such as a chromosomal, mitochondrial, chloroplast, viral, extra chromosomal, or mycoplasmal polynucleotide). By "corresponds to" herein is meant that a polynucleotide sequence is homologous (i.e., may be similar or identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence can hybridize to all or a portion of a reference polynucleotide sequence. Thus, one of the complementary single stranded targeting polynucleotides is complementary to one strand of the endogenous target consensus sequence (i.e. Watson) and corresponds to the other strand of the endogenous target consensus sequence (i.e. Crick). Thus, the complementarity between two single-stranded targeting polynucleotides need not be perfect. For illustration, the nucleotide sequence "TATAC" corresponds to a reference sequence "TATAC" and is perfectly complementary to a reference sequence "GTATA".

The terms "substantially corresponds to" or "substantial identity" or "homologous" as used herein denotes a characteristic of a nucleic acid sequence, wherein a nucleic acid sequence has at least about 50 percent sequence identity as compared to a reference sequence, typically at least about 70 percent sequence identity, and preferably at least about 85 percent sequence identity as compared to a reference sequence. The percentage of sequence identity is calculated excluding small deletions or additions which total less than 25 percent of the reference sequence. The reference sequence may be a subset of a larger sequence, such as a portion of a gene or flanking sequence, or a repetitive portion of a chromosome. However, the reference sequence is at least 18 nucleotides long, typically at least about 30 nucleotides long, and preferably at least about 50 to 100 nucleotides long. "Substantially complementary" as used herein refers to a sequence that is complementary to a sequence that substantially corresponds to a reference sequence. In general, targeting efficiency increases with the length of the targeting polynucleotide portion that is substantially complementary to a reference sequence present in the target DNA.

These corresponding/complementary sequences are referred to herein as "consensus homology clamps", as they serve as templates for homologous pairing with the predetermined endogenous sequence(s). Thus, a "consensus homology clamp" is a portion of the targeting polynucleotide that can specifically hybridize to a consensus functional domain within a gene of interest. "Specific hybridization" is defined herein as the formation of hybrids between a targeting polynucleotide (e.g., a polynucleotide of the invention which may include substitutions, deletion, and/or additions as compared to the predetermined target nucleic acid sequence) and a predetermined target nucleic acid, wherein the targeting polynucleotide preferentially hybridizes to the predetermined target nucleic acid such that, for example, at least one discrete band can be identified on a Southern blot of nucleic acid prepared from target cells that contain the target nucleic acid sequence, and/or a targeting polynucleotide in an intact nucleus localizes to a discrete chromosomal location characteristic of a unique or repetitive sequence. As will be appreciated by those in the art, a target consensus functional domain sequence may be present in more than one target polynucleotide species (e.g., a particular target sequence may occur in multiple members of a gene family). It is evident that optimal hybridization conditions will vary depending upon the sequence composition and length(s) of the targeting polynucleotide(s) and target(s), and the experimental method selected by the practitioner. Various guidelines may be used to select appropriate hybridization conditions (see, Maniatis et al., *Molecular Cloning: A Laboratory Manual* (1989), 2nd Ed., Cold Spring Harbor, N.Y. and Berger and Kimmel, *Methods in Enzymology, Volume* 152, *Guide to Molecular Cloning Techniques* (1987), Academic Press, Inc., San Diego, Calif.), which are incorporated herein by reference. Methods for hybridizing a targeting polynucleotide to a discrete chromosomal location in intact nuclei are known in the art, see for example WO 93/05177 and Kowalczykowski and Zarling (1994) in Gene Targeting, Ed. Manuel Vega.

In targeting polynucleotides, such consensus homology clamps are typically located at or near the 5' or 3' end, preferably consensus homology clamps are internal or located at each end of the polynucleotide (Berinstein et al. (1992) *Molec. Cell. Biol.* 12: 360, which is incorporated herein by reference). Without wishing to be bound by any particular theory, it is believed that the addition of recombinases permits efficient gene targeting with targeting polynucleotides having short (i.e., about 10 to 1000 basepair long) segments of homology, as well as with targeting polynucleotides having longer segments of homology.

Therefore, it is preferred that targeting polynucleotides of the invention have consensus homology clamps that are highly homologous to the predetermined target endogenous consensus functional domain nucleic acid sequence(s).

Typically, targeting polynucleotides of the invention have at least one consensus homology clamp that is at least about 18 to 35 nucleotides long, and it is preferable that consensus homology clamps are at least about 20 to 100 nucleotides long, and more preferably at least about 100–500 nucleotides long, although the degree of sequence homology between the consensus homology clamp and the targeted sequence and the base composition of the targeted sequence will determine the optimal and minimal clamp lengths (e.g., G-C rich sequences are typically more thermodynamically stable and will generally require shorter clamp length). Therefore, both consensus homology clamp length and the degree of sequence homology can only be determined with reference to a particular predetermined consensus sequence, but consensus homology clamps generally must be at least about 10 nucleotides long and must also substantially correspond or be substantially complementary to a predetermined consensus target sequence. Preferably, a homology clamp is at least about 10, and preferably at least about 50 nucleotides long and is substantially identical to or complementary to a predetermined target sequence. Without wishing to be bound by a particular theory, it is believed that the addition of recombinases to a targeting polynucleotide enhances the efficiency of homologous recombination between homologous, nonisogenic sequences (e.g., between an exon 2 sequence of an albumin gene of a Balb/c mouse and a homologous albumin gene exon 2 sequence of a C57/BL6 mouse), as well as between isogenic sequences.

The formation of heteroduplex joints is not a stringent process; genetic evidence supports the view that the classical phenomena of meiotic gene conversion and aberrant meiotic segregation results in part from the inclusion of mismatched base pairs in heteroduplex joints, and the subsequent correction of some of these mismatched base pairs before replication. Observations on recA protein have provided information on parameters that affect the discrimination of relatedness from perfect or near-perfect homology and that affect the inclusion of mismatched base pairs in heteroduplex joints. The ability of recA protein to drive strand exchange past all single base-pair mismatches and to form extensively mismatched joints in superhelical DNA reflect its role in recombination and gene conversion. This error-prone process may also be related to its role in mutagenesis. RecA-mediated pairing reactions involving DNA of φX174 and G4, which are about 70 percent homologous, have yielded homologous recombinants (Cunningham et al. (1981) *Cell* 24: 213), although recA preferentially forms homologous joints between highly homologous sequences, and is implicated as mediating a homology search process between an invading DNA strand and a recipient DNA strand, producing relatively stable heteroduplexes at regions of high homology. Accordingly, it is the fact that recombinases can drive the homologous recombination reaction between strands which are significantly, but not perfectly, homologous, which allows gene conversion and the modification of target sequences. Thus, targeting polynucleotides may be used to introduce nucleotide substitutions, insertions and deletions into an endogenous consensus functional domain nucleic acid sequence, and thus the corresponding amino acid substitutions, insertions and deletions in proteins expressed from the endogenous consensus functional domain nucleic acid sequence. By "endogenous" in this context herein is meant the naturally occurring sequence, i.e. sequences or substances originating from within a cell or organism. Similarly, "exogenous" refers to sequences or substances originating outside the cell or organism.

In a preferred embodiment, two substantially complementary targeting polynucleotides are used. In one embodiment, the targeting polynucleotides form a double stranded hybrid, which may be coated with recombinase, although when the recombinase is recA, the loading conditions may be somewhat different from those used for single stranded nucleic acids.

In a preferred embodiment, two substantially complementary single-stranded targeting polynucleotides are used. The two complementary single-stranded targeting polynucleotides are usually of equal length, although this is not required. However, as noted below, the stability of the four strand hybrids of the invention is putatively related, in part, to the lack of significant unhybridized single-stranded nucleic acid, and thus significant unpaired sequences are not preferred. Furthermore, as noted above, the complementarity between the two targeting polynucleotides need not be perfect. The two complementary single-stranded targeting polynucleotides are simultaneously or contemporaneously introduced into a target cell harboring a predetermined endogenous target sequence, generally with at lease one recombinase protein (e.g., recA). Under most circumstances, it is preferred that the targeting polynucleotides are incubated with recA or other recombinase prior to introduction into a target cell, so that the recombinase protein(s) may be "loaded" onto the targeting polynucleotide(s), to coat the nucleic acid, as is described below. Incubation conditions for such recombinase loading are described infra, and also in U.S. Ser. No. 07/1755,462, filed Sep. 4, 1991 now U.S. Pat. No. 5,273,881; U.S. Ser. No. 07/910,791, filed Jul. 9, 1992 now abandoned; and U.S. Ser. No. 07/520,321, filed May 7, 1990 now U.S. Pat. No. 5,223,414, each of which is incorporated herein by reference. A targeting polynucleotide may contain a sequence that enhances the loading process of a recombinase, for example a recA loading sequence is the recombinogenic nucleation sequence poly[d(A-C)], and its complement, poly[d(G-T)]. The duplex sequence poly[d(A-C). d(G-T)$_n$, where n is from 5 to 25, is a middle repetitive element in target DNA.

There appears to be a fundamental difference in the stability of RecA-protein-mediated D-loops formed between one single-stranded DNA (ssDNA) probe hybridized to negatively supercoiled DNA targets in comparison to relaxed or linear duplex DNA targets. Internally located dsDNA target sequences on relaxed linear DNA targets hybridized by ssDNA probes produce single D-loops, which are unstable after removal of RecA protein (Adzuma, Genes Devel. 6:1679 (1992); Hsieh et al, PNAS USA 89:6492 (1992); Chiu et al., Biochemistry 32:13146 (1993)). This probe DNA instability of hybrids formed with linear duplex DNA targets is most probably due to the incoming ssDNA probe W-C base pairing with the complementary DNA strand of the duplex target and disrupting the base pairing in the other DNA strand. The required high free-energy of maintaining a disrupted DNA strand in an unpaired ssDNA conformation in a protein-free single-D-loop apparently can only be compensated for either by the stored free energy inherent in negatively supercoiled DNA targets or by base pairing initiated at the distal ends of the joint DNA molecule, allowing the exchanged strands to freely intertwine.

However, the addition of a second complementary ssDNA to the three-strand-containing single-D-loop stabilizes the deproteinized hybrid joint molecules by allowing W-C base pairing of the probe with the displaced target DNA strand. The addition of a second RecA-coated complementary ssDNA (cssDNA) strand to the three-strand containing single D-loop stabilizes deproteinized hybrid joints located away from the free ends of the duplex target DNA (Sena & Zarling, Nature Genetics 3:365 (1993); Revet et al. J. Mol.

Biol. 232:779 (1993); Jayasena and Johnston, J. Mol. Bio. 230:1015 (1993)). The resulting four-stranded structure, named a double D-loop by analogy with the three-stranded single D-loop hybrid has been shown to be stable in the absence of RecA protein. This stability likely occurs because the restoration of W-C basepairing in the parental duplex would require disruption of two basepairs in the double-D-loop (one W-C pair in each heteroduplex D-loop). Since each base-pairing in the reverse transition (double-D-loop to duplex) is less favorable by the energy of one W-C basepair, the pair of cssDNA probes are thus kinetically trapped in duplex DNA targets in stable hybrid structures. The stability of the double-D loop joint molecule within internally located probe:target hybrids is an intermediate stage prior to the progression of the homologous recombination reaction to the strand exchange phase. The double D-loop permits isolation of stable multistranded DNA recombination intermediates.

The invention may also be practiced with individual targeting polynucleotides which do not comprise part of a complementary pair. In each case, a targeting polynucleotide is introduced into a target cell simultaneously or contemporaneously with a recombinase protein, typically in the form of a recombinase coated targeting polynucleotide as outlined herein (i.e., a polynucleotide pre-incubated with recombinase wherein the recombinase is noncovalently bound to the polynucleotide; generally referred to in the art as a nucleoprotein filament).

The present invention allows for the introduction of alterations in the target nucleic acid consensus functional domain of a member of a gene family. That is, the fact that heterologies are tolerated in targeting polynucleotides allows for two things: first, the use of a heterologous consensus homology clamp that may target consensus functional domains of multiple genes, rather than a single gene, resulting in a variety of genotypes and phenotypes, and secondly, the introduction of alterations to the target sequence. Thus typically, a targeting polynucleotide (or complementary polynucleotide pair) has a portion or region having a sequence that is not present in the preselected endogenous targeted sequence(s) (i.e., a nonhomologous portion or mismatch) which may be as small as a single mismatched nucleotide, several mismatches, or may span up to about several kilobases or more of nonhomologous sequence.

Accordingly, in a preferred embodiment, the methods and compositions of the invention are used for inactivation of a gene family gene. That is, exogenous targeting polynucleotides can be used to inactivate, decrease or alter the biological activity of one or more genes in a cell (or transgenic nonhuman animal or plant). This finds particular use in the generation of animal models of disease states, or in the elucidation of gene function and activity, similar to "knock out" experiments. Alternatively, the biological activity of the wild-type gene may be either decreased, or the wild-type activity altered to mimic disease states. This includes genetic manipulation of non-coding gene sequences that affect the transcription of genes, including, promoters, repressors, enhancers and transcriptional activating sequences.

Thus in a preferred embodiment, homologous recombination of the targeting polynucleotide and endogenous target sequence will result in amino acid substitutions, insertions or deletions in the endogenous target sequences, potentially both within the consensus functional domain region and outside of it, for example as a result of the incorporation of PCR tags. This will generally result in modulated or altered gene function of the endogenous gene, including both a decrease or elimination of function as well as an enhancement of function. Nonhomologous portions are used to make insertions, deletions, and/or replacements in a predetermined endogenous targeted DNA sequence, and/or to make single or multiple nucleotide substitutions in a predetermined endogenous target DNA sequence so that the resultant recombined sequence (i.e., a targeted recombinant endogenous sequence) incorporates some or all of the sequence information of the nonhomologous portion of the targeting polynucleotide(s). Thus, the nonhomologous regions are used to make variant sequences, i.e. targeted sequence modifications. In this way, site directed modifications may be done in a variety of systems for a variety of purposes.

The endogenous target sequence, generally a consensus functional domain, may be disrupted in a variety of ways. The term "disrupt" as used herein comprises a change in the coding or non-coding sequence of an endogenous nucleic acid. In one preferred embodiment, a disrupted gene will no longer produce a functional gene product. In another preferred embodiment, a disrupted gene produces a variant gene product Generally, disruption may occur by either the substitution, insertion, deletion or frame shifting of nucleotides.

In one embodiment, amino acid substitutions are made. This can be the result of either the incorporation of a non-naturally occurring consensus sequence into a consensus target, or of more specific changes to a particular sequence outside of the consensus sequence.

In one embodiment, the endogenous sequence is disrupted by an insertion sequence. The term "insertion sequence" as used herein means one or more nucleotides which are inserted into an endogenous gene to disrupt it. In general, insertion sequences can be as short as 1 nucleotide or as long as a gene, as outlined herein. For non-gene insertion sequences, the sequences are at least 1 nucleotide, with from about 1 to about 50 nucleotides being preferred, and from about 10 to 25 nucleotides being particularly preferred. An insertion sequence may comprise a polylinker sequence, with from about 1 to about 50 nucleotides being preferred, and from about 10 to 25 nucleotides being particularly preferred. Insertion sequence may be a PCR tag used for identification of the first gene.

In a preferred embodiment, an insertion sequence comprises a gene which not only disrupts the endogenous gene, thus preventing its expression, but also can result in the expression of a new gene product. Thus, in a preferred embodiment, the disruption of an endogenous gene by an insertion sequence gene is done in such a manner to allow the transcription and translation of the insertion gene. An insertion sequence that encodes a gene may range from about 50 bp to 5000 bp of cDNA or about 5000 bp to 50000 bp of genomic DNA. As will be appreciated by those in the art, this can be done in a variety of ways. In a preferred embodiment, the insertion gene is targeted to the endogenous gene in such a manner as to utilize endogenous regulatory sequences, including promoters, enhancers or a regulatory sequence. In an alternate embodiment, the insertion sequence gene includes its own regulatory sequences, such as a promoter, enhancer or other regulatory sequence etc.

Particularly preferred insertion sequence genes include, but are not limited to, genes which encode selection or reporter proteins. In addition, the insertion sequence genes may be modified or variant genes.

The term "deletion" as used herein comprises removal of a portion of the nucleic acid sequence of an endogenous gene. Deletions range from about 1 to about 100 nucleotides, with from about 1 to 50 nucleotides being preferred and from about 1 to about 25 nucleotides being particularly preferred, although in some cases deletions may be much larger, and may effectively comprise the removal of the entire consensus functional domain, the entire endogenous gene and/or its regulatory sequences. Deletions may occur in combination with substitutions or modifications to arrive at a final modified endogenous gene.

In a preferred embodiment, endogenous genes may be disrupted simultaneously by an insertion and a deletion. For example, some or all of an endogenous gene, with or without its regulatory sequences, may be removed and replaced with an insertion sequence gene. Thus, for example, all but the regulatory sequences of an endogenous gene may be removed, and replaced with an insertion sequence gene, which is now under the control of the endogenous gene's regulatory elements.

The term "regulatory element" is used herein to describe a non-coding sequence which affects the transcription or translation of a gene including, but are not limited to, promoter sequences, ribosomal binding sites, transcriptional start and stop sequences, translational start and stop sequences, enhancer or activator sequences, dimerizing sequences, etc. In a preferred embodiment, the regulatory sequences include a promoter and transcriptional start and stop sequence. Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, when the targeting polynucleotides are used to generate insertions or deletions in an endogenous nucleic acid sequence, as is described herein, the use of two complementary single-stranded targeting polynucleotides allows the use of internal homology clamps as depicted in the figures of PCT US98/05223. The use of internal homology clamps allows the formation of stable deproteinized cssDNA:probe target hybrids with homologous DNA sequences containing either relatively small or large insertions and deletions within a homologous DNA target. Without being bound by theory, it appears that these probe:target hybrids, with heterologous inserts in the cssDNA probe, are stabilized by the re-annealing of cssDNA probes to each other within the double-D-loop hybrid, forming a novel DNA structure with an internal homology clamp. Similarly stable double-D-loop hybrids formed at internal sites with heterologous inserts in the linear DNA targets (with respect to the cssDNA probe) are equally stable. Because cssDNA probes are kinetically trapped within the duplex target, the multi-stranded DNA intermediates of homologous DNA pairing are stabilized and strand exchange is facilitated.

In a preferred embodiment, the length of the internal homology clamp (i.e. the length of the insertion or deletion) is from about 1 to 50% of the total length of the targeting polynucleotide, with from about 1 to about 20% being preferred and from about 1 to about 10% being especially preferred, although in some cases the length of the deletion or insertion may be significantly larger. As for the consensus homology clamps, the complementarity within the internal homology clamp need not be perfect.

A targeting polynucleotide used in a method of the invention typically is a single-stranded nucleic acid, usually a DNA strand, or derived by denaturation of a duplex DNA, which is complementary to one (or both) strand(s) of the target duplex nucleic acid. Thus, one of the complementary single stranded targeting polynucleotides is complementary to one strand of the endogenous target sequence (i.e. Watson) and the other complementary single stranded targeting polynucleotide is complementary to the other strand of the endogenous target sequence (i.e. Crick). The consensus homology clamp sequence preferably contains at least 90–95% sequence homology with the target sequence (although as outlined above, less sequence homology can be tolerated), to insure sequence-specific targeting of the targeting polynucleotide to the endogenous DNA consensus target. Each single-stranded targeting polynucleotide is typically about 50–600 bases long, although a shorter or longer polynucleotide may also be employed.

Once the gene family and consensus sequence is selected, the targeting polynucleotides are made, as will be appreciated by those in the art. For example, for large targeting polynucleotides, plasmids are engineered to contain an appropriately sized gene sequence with a deletion or insertion in the gene of interest and at least one flanking homology clamp which substantially corresponds or is substantially complementary to an endogenous target DNA sequence. Vectors containing a targeting polynucleotide sequence are typically grown in *E. coli* and then isolated using standard molecular biology methods. Alternatively, targeting polynucleotides may be prepared in single-stranded form by oligonucleotide synthesis methods, which may first require, especially with larger targeting polynucleotides, formation of subfragments of the targeting polynucleotide, typically followed by splicing of the subfragments together, typically by enzymatic ligation. In general, as will be appreciated by those in the art, targeting polynucleotides may be produced by chemical synthesis of oligonucleotides, nick-translation of a double-stranded DNA template, polymerase chain-reaction amplification of a sequence (or ligase chain reaction amplification), purification of prokaryotic or target cloning vectors harboring a sequence of interest (e.g., a cloned cDNA or genomic clone, or portion thereof) such as plasmids, phagemids, YACs, cosmids, bacteriophage DNA, other viral DNA or replication intermediates, or purified restriction fragments thereof, as well as other sources of single and double-stranded polynucleotides having a desired nucleotide sequence. When using microinjection procedures it may be preferable to use a transfection technique with linearized sequences containing only modified target gene sequence and without vector or selectable sequences. The modified gene site is such that a homologous recombinant between the exogenous targeting polynucleotide and the endogenous DNA target sequence can be identified by using carefully chosen primers and PCR, followed by analysis to detect if PCR products specific to the desired targeted event are present (Erlich et al., (1991) *Science* 252: 1643, which is incorporated herein by reference). Several studies have already used PCR to successfully identify and then clone the desired transfected cell lines (Zimmer and Gruss, (1989) *Nature* 338: 150; Mouellic et al., (1990) *Proc. Natl. Acad. Sci. USA* 87: 4712; Shesely et al., (1991) *Proc. Natl. Acad. Sci. USA* 88: 4294, which are incorporated herein by reference). This approach is very effective when the number of cells receiving exogenous targeting polynucleotide(s) is high (i.e., with microinjection, or with liposomes) and the treated cell populations are allowed to expand to cell groups of approximately $1 \times 10^4$ cells (Capecchi, (1989) *Science* 244: 1288). When the target gene is not on a sex chromosome, or the cells are derived from a female; both alleles of a gene can be targeted by sequential inactivation (Mortensen et al., (1991)

*Proc. Natl. Acad. Sci. USA* 88: 7036). Alternatively, animals heterologous for the target gene can be bred to homologously as is known in the art.

In addition to consensus homology clamps and optional internal homology clamps, the targeting polynucleotides of the invention may comprise additional components, such as cell-uptake components, chemical substituents, purification tags, etc.

In a preferred embodiment, at least one of the targeting polynucleotides comprises at least one cell-uptake component. As used herein, the term "cell-uptake component" refers to an agent which, when bound, either directly or indirectly, to a targeting polynucleotide, enhances the intracellular uptake of the targeting polynucleotide into at least one cell type (e.g., hepatocytes). A targeting polynucleotide of the invention may optionally be conjugated, typically by covalently or preferably noncovalent binding, to a cell-uptake component. Various methods have been described in the art for targeting DNA to specific cell types. A targeting polynucleotide of the invention can be conjugated to essentially any of several cell-uptake components known in the art. For targeting to hepatocytes, a targeting polynucleotide can be conjugated to an asialoorosomucoid (ASOR)-poly-L-lysine conjugate by methods described in the art and incorporated herein by reference (Wu GY and Wu CH (1987) *J. Biol. Chem.* 262:4429; Wu GY and Wu CH (1988) *Biochemistry* 27:887; Wu GY and Wu CH (1988) *J. Biol. Chem.* 263:14621; Wu GY and Wu CH (1992) *J. Biol. Chem.* 267:12436; Wu et al. (1991) *J. Biol. Chem.* 266:14338; and Wilson et al. (1992) *J. Biol. Chem.* 267: 963, WO92/06180; WO92105250; and WO91/17761, which are incorporated herein by reference).

Alternatively, a cell-uptake component may be formed by incubating the targeting polynucleotide with at least one lipid species and at least one protein species to form protein-lipid-polynucleotide complexes consisting essentially of the targeting polynucleotide and the lipid-protein cell-uptake component. Lipid vesicles made according to Feigner (WO91/17424, incorporated herein by reference) and/or cationic lipidization (WO91/16024, incorporated herein by reference) or other forms for polynucleotide administration (EP 465,529, incorporated herein by reference) may also be employed as cell-uptake components. Nucleases may also be used.

In addition to cell-uptake components, targeting components such as nuclear localization signals may be used, as is known in the art. See for example Kido et al., Exper. Cell Res. 198:107–114 (1992), hereby expressly incorporated by reference.

Typically, a targeting polynucleotide of the invention is coated with at least one recombinase and is conjugated to a cell-uptake component, and the resulting cell targeting complex is contacted with a target cell under uptake conditions (e.g., physiological conditions) so that the targeting polynucleotide and the recombinase(s) are internalized in the target cell. A targeting polynucleotide may be contacted simultaneously or sequentially with a cell-uptake component and also with a recombinase; preferably the targeting polynucleotide is contacted first with a recombinase, or with a mixture comprising both a cell-uptake component and a recombinase under conditions whereby, on average, at least about one molecule of recombinase is noncovalently attached per targeting polynucleotide molecule and at least about one cell-uptake component also is noncovalently attached. Most preferably, coating of both recombinase and cell-uptake component saturates essentially all of the available binding sites on the targeting polynucleotide. A targeting polynucleotide may be preferentially coated with a cell-uptake component so that the resultant targeting complex comprises, on a molar basis, more cell-uptake component than recombinase(s). Alternatively, a targeting polynucleotide may be preferentially coated with recombinase(s) so that the resultant targeting complex comprises, on a molar basis, more recombinase(s) than cell-uptake component.

Cell-uptake components are included with recombinase-coated targeting polynucleotides of the invention to enhance the uptake of the recombinase-coated targeting polynucleotide(s) into cells, particularly for in vivo gene targeting applications, such as gene therapy to treat genetic diseases, including neoplasia, and targeted homologous recombination to treat viral infections wherein a viral sequence (e.g., an integrated hepatitis B virus (HBV) genome or genome fragment) may be targeted by homologous sequence targeting and inactivated. Alternatively, a targeting polynucleotide may be coated with the cell-uptake component and targeted to cells with a contemporaneous or simultaneous administration of a recombinase (e.g., liposomes or immunoliposomes containing a recombinase, a viral-based vector encoding and expressing a recombinase).

In addition to recombinase and cellular uptake components, at least one of the targeting polynucleotides may include chemical substituents. Exogenous targeting polynucleotides that have been modified with appended chemical substituents may be introduced along with recombinase (e.g., recA) into a metabolically active target cell to homologously pair with a predetermined endogenous DNA target sequence in the cell. In a preferred embodiment, the exogenous targeting polynucleotides are derivatized, and additional chemical substituents are attached, either during or after polynucleotide synthesis, respectively, and are thus localized to a specific endogenous target sequence where they produce an alteration or chemical modification to a local DNA sequence. Preferred attached chemical substituents include, but are not limited to: cross-linking agents (see Podyminogin et al., Biochem. 34:13098 (1995) and 35:7267 (1996), both of which are hereby incorporated by reference), nucleic acid cleavage agents, metal chelates (e.g., iron/EDTA chelate for iron catalyzed cleavage), topoisomerases, endonucleases, exonucleases, ligases, phosphodiesterases, photodynamic porphyrins, chemotherapeutic drugs (e.g., adriamycin, doxirubicin), intercalating agents, labels, base-modification agents, agents which normally bind to nucleic acids such as labels, etc. (see for example Afonina et al., PNAS USA 93:3199 (1996), incorporated herein by reference) immunoglobulin chains, and oligonucleotides. Iron/EDTA chelates are particularly preferred chemical substituents where local cleavage of a DNA sequence is desired (Hertzberg et al. (1982) *J. Am. Chem. Soc.* 104: 313; Hertzberg and Dervan (1984) *Biochemistry* 23: 3934; Taylor et al. (1984) *Tetrahedron* 40: 457; Dervan, P B (1986) *Science* 232: 464, which are incorporated herein by reference). Further preferred are groups that prevent hybridization of the complementary single stranded nucleic acids to each other but not to unmodified nucleic acids; see for example Kutryavin et al., Biochem. 35:11170 (1996) and Woo et al., Nucleic Acid. Res. 24(13):2470 (1996), both of which are incorporated by reference. 2'-O methyl groups are also preferred; see Cole-Strauss et al., Science 273:1386 (1996); Yoon et al., PNAS 93:2071 (1996)). Additional preferred chemical substituents include labeling moieties, including fluorescent labels. Preferred attachment chemistries include: direct linkage, e.g., via an appended reactive amino group (Corey and Schultz (1988) *Science* 238:1401, which is incorporated herein by reference) and other direct linkage chemistries, although streptavidin/biotin and digoxigenin/antidigoxigenin antibody linkage methods may also be used. Methods for linking chemical substituents are provided in U.S. Pat. Nos. 5,135,720, 5,093,245, and 5,055,556, which are incorporated herein by reference. Other linkage chemistries may be used at the discretion of the practitioner.

In a preferred embodiment, at least one of the targeting polynucleotides comprises at least one purification tag or capture moiety, some of which are discussed above as chemical substituents, for example biotin, digoxigenin, psoralen, etc. Alternatively, the consensus oligonucleotide could be directly attached to beads with the targeting reaction performed on a solid phase support.

In a preferred embodiment, the targeting polynucleotides are coated with recombinase prior to introduction to the consensus target. The conditions used to coat targeting polynucleotides with recombinases such as recA protein and ATPγS have been described in commonly assigned U.S. Ser. No. 07/910,791, filed Jul. 9, 1992 now abandoned; U.S. Ser .No. 07/755,462, filed Sep. 4, 1991 now U.S. Pat. No. 5,273,881; and U.S. Ser. No. 07/520,321, filed May 7, 1990 U.S. Pat. No. 5,223,414 now , and PCT US98/05223, each incorporated herein by reference. The procedures below are directed to the use of E. coli recA, although as will be appreciated by those in the art, other recombinases may be used as well. Targeting polynucleotides can be coated using GTPγS, mixes of ATPγS with rATP, rGTP and/or dATP, or dATP or rATP alone in the presence of an rATP generating system (Boeh ringer Mannheim). Various mixtures of GTPγS, ATPγS, ATP, ADP, dATP and/or rATP or other nucleosides may be used, particularly preferred are mixes of ATPγS and ATP or ATPγS and ADP.

RecA protein coating of targeting polynucleotides is typically carried out as described in U.S. Ser. No. 07/910,791, filed Jul. 9, 1992 now abandoned and U.S. Ser. No. 07/755,462, filed Sep. 4, 1991 now U.S. Pat. No. 5,273,881, and PCT US98/05223, which are incorporated herein by reference. Briefly, the targeting polynucleotide, whether double-stranded or single-stranded, is denatured by heating in an aqueous solution at 95–100° C. for five minutes, then placed in an ice bath for 20 seconds to about one minute followed by centrifugation at 0° C. for approximately 20 sec, before use. When denatured targeting polynucleotides are not placed in a freezer at –20° C. they are usually immediately added to standard recA coating reaction buffer containing ATPγS, at room temperature, and to this is added the recA protein. Alternatively, recA protein may be included with the buffer components and ATPγS before the polynucleotides are added.

RecA coating of targeting polynucleotide(s) is initiated by incubating polynucleotide-recA mixtures at 37° C. for 10–15 min. RecA protein concentration tested during reaction with polynucleotide varies depending upon polynucleotide size and the amount of added polynucleotide, and the ratio of recA molecule:nucleotide preferably ranges between about 3:1 and 1:3. When single-stranded polynucleotides are recA coated independently of their homologous polynucleotide strands, the mM and μM concentrations of ATPγS and recA, respectively, can be reduced to one-half those used with double-stranded targeting polynucleotides (i.e., recA and ATPγS concentration ratios are usually kept constant at a specific concentration of individual polynucleotide strand, depending on whether a single-or double-stranded polynucleotide is used).

RecA protein coating of targeting polynucleotides is normally carried out in a standard 1×RecA coating reaction buffer. 10×RecA reaction buffer (i.e., 10×AC buffer) consists of: 100 mM Tris acetate (pH 7.5 at 37° C.), 20 mM magnesium acetate, 500 mM sodium acetate, 10 mM DTT, and 50% glycerol). All of the targeting polynucleotides, whether double-stranded or single-stranded, typically are denatured before use by heating to 95–100° C. for five minutes, placed on ice for one minute, and subjected to centrifugation (10,000 rpm) at 0° C. for approximately 20 seconds (e.g., in a Tomy centrifuge). Denatured targeting polynucleotides usually are added immediately to room temperature RecA coating reaction buffer mixed with ATPγS and diluted with double-distilled $H_2O$ as necessary.

A reaction mixture typically contains the following components: (i) 0.2–4.8 mM ATPγS; and (ii) between 1–100 ng/μl of targeting polynucleotide. To this mixture is added about 1–20 μl of recA protein per 10–100 μl of reaction mixture, usually at about 2–10 mg/ml (purchased from Pharmacia or purified), and is rapidly added and mixed. The final reaction volume-for RecA coating of targeting polynucleotide is usually in the range of about 10–500 μl. RecA coating of targeting polynucleotide is usually initiated by incubating targeting polynucleotide-RecA mixtures at 37° C. for about 10–15 min.

RecA protein concentrations in coating reactions varies depending upon targeting polynucleotide size and the amount of added targeting polynucleotide: recA protein concentrations are typically in the range of 5 to 50 μM. When single-stranded targeting polynucleotides are coated with recA, independently of their complementary strands, the concentrations of ATPγS and recA protein may optionally be reduced to about one-half of the concentrations used with double-stranded targeting polynucleotides of the same length: that is, the recA protein and ATPγS concentration ratios are generally kept constant for a given concentration of individual polynucleotide strands.

The coating of targeting polynucleotides with recA protein can be evaluated in a number of ways. First, protein binding to DNA can be examined using band-shift gel assays (McEntee et al., (1981) J. Biol. Chem. 256: 8835). Labeled polynucleotides can be coated with recA protein in the presence of ATPγS and the products of the coating reactions may be separated by agarose gel electrophoresis. Following incubation of recA protein with denatured duplex DNAs the recA protein effectively coats single-stranded targeting polynucleotides derived from denaturing a duplex DNA. As the ratio of recA protein monomers to nucleotides in the targeting polynucleotide increases from 0, 1:27, 1:2.7 to 3.7:1 for 121-mer and 0, 1:22, 1:2.2 to 4.5:1 for 159-mer, targeting polynucleotide's electrophoretic mobility decreases, i.e., is retarded, due to recA-binding to the targeting polynucleotide. Retardation of the coated polynucleotide's mobility reflects the saturation of targeting polynucleotide with recA protein. An excess of recA monomers to DNA nucleotides is required for efficient recA coating of short targeting polynucleotides (Leahy et al., (1986) J. Biol. Chem. 261: 954).

A second method for evaluating protein binding to DNA is in the use of nitrocellulose fiber binding assays (Leahy et al., (1986) J. Biol. Chem. 261:6954; Woodbury, et al., (1983) Biochemistry 22(20):47304737. The nitrocellulose filter binding method is particularly useful in determining the dissociation-rates for protein:DNA complexes using labeled DNA. In the filter binding assay, DNA:protein complexes are retained on a filter while free DNA passes through the filter. This assay method is more quantitative for dissociation-rate determinations because the separation of DNA:protein complexes from free targeting polynucleotide is very rapid.

Alternatively, recombinase protein(s) (prokaryotic, eukaryotic or endogenous to the target cell) may be exogenously induced or administered to a target cell simultaneously or contemporaneously (i.e., within about a few hours) with the targeting polynucleotide(s). Such administration is typically done by micro-injection, although electroporation, lipofection, and other transfection methods known in the art may also be used. Alternatively, recombinase-proteins may be produced in vivo. For example, they may be produced from a homologous or heterologous expression cassette in a transfected cell or targeted cell, such as a transgenic totipotent cell (e.g. a fertilized zygote) or an embryonal stem cell (e.g., a murine ES cell such as AB-1) used to generate a transgenic non-human animal line or a somatic cell or a pluripotent hematopoietic stem cell for reconstituting all or part of a particular stem cell population (e.g. hematopoietic) of an individual. Conveniently, a heterologous expression cassette includes a modulatable promoter, such as an ecdysone-inducible promoter-enhancer combination, an estrogen-induced promoter-enhancer combination, a CMV promoter-enhancer, an insulin gene promoter, or other cell-type specific, developmental stage-specific, hormone-inducible drug inducible, such as tetra or other modulatable promoter construct so that expression of at least one species of recombinase protein from the cassette can by modulated for transiently producing recombinase(s) in vivo simultaneous or contemporaneous with introduction of a targeting polynucleotide into the cell. When a hormone-inducible promoter-enhancer combination is used, the cell must have the required hormone receptor present, either naturally or as a consequence of expression a co-transfected expression vector encoding such receptor. Alternatively, the recombinase may be endogenous and produced in high levels. In this embodiment, preferably in eukaryotic target cells such as tumor cells, the target cells produce an elevated level of recombinase. In other embodiments the level of recombinase may be induced by DNA damaging agents, such as mitomycin C, UV or γ-irradiation. Alternatively, recombinase levels may be elevated by transfection of a plasmid encoding the recombinase gene into the cell.

Once made, the compositions of the invention find use in a number of applications upon administration to target cells. In general, the compositions and methods of the invention are useful to identify new members of gene families which may be useful in functional genomic studies as well as in the identification of new drug targets; both of these may be accomplished through the generation of "knock out" animal models. In addition, the present invention allows the modification of consensus functional domain targets, the creation of transgenic plants and animals, the cloning of genes containing consensus functional domains, etc.

In a preferred embodiment, the present invention finds use in the isolation of new members of gene families. As is generally depicted in FIG. 2, the use of HMT filaments (i.e. consensus homology clamps preferably containing a purification tag such as biotin, disoxisenin, or one purification method such as the use of a recA antibody), allows the identification of new genes within the gene family. Once identified, the new genes can be cloned, sequenced and the protein gene products purified. As will be appreciated by those in the art, the functional importance of the new genes can be assessed in a number of ways, including functional studies on the protein level, as well as the generation of "knock out" animal models. By choosing consensus sequences for therapeutically relevant gene families, novel targets can be identified that can be used in screening of drug candidates.

Thus, in a preferred embodiment, the present invention provides methods for isolating new members of gene families comprising introducing targeting polynucleotides comprising consensus homology clamps and at least one purification tag, preferably biotin, to a mix of nucleic acid, such as a plasmid cDNA library or a cell, and then utilizing the purification tag to isolate the gene(s). The exact methods will depend on the purification tag; a preferred method utilizes the attachment of the binding ligand for the tag to a bead, which is then used to pull out the sequence. Alternatively anti-recA antibodies could be used to capture recA-coated probes. The genes are then cloned, sequenced, and reassembled if necessary, as is well known in the art.

In an alternate preferred embodiment, the present invention finds use in functional genomic studies, by providing the creation of transgenic animal models of disease. Thus, for example, HMTs used in homologous recombination methods can generate animals that have a wide variety of mutations in a wide variety of related genes, potentially resulting in a wide variety of phenotypes, including phenotypes related to disease states. That is, by targeting a gene family, one, two or multiple genes in the family may be altered in any given experiment, thus creating a wide variety of genotypes and phenotypes to evaluate. Thus, in a preferred embodiment, the compositions and methods of the invention are used to generate pools or libraries of variant nucleic acid sequences, wherein the mutations are within the consensus functional domain coding region, cellular libraries containing the variant libraries, and libraries of animals containing the variant libraries.

Furthermore, HMT targeting can be used in cells or animals that are diseased or altered; in essence, HMT targeting can be done to identify "reversion" genes, genes that can modulate disease states caused by different genes, either genes within the same gene family or a completely different gene family. Thus for example the loss of one type of enzymatic activity, resulting in a disease phenotype, may be compensated by alterations in a different but homologous enzymatic activity.

Accordingly, once the recombinase-targeting polynucleotide compositions are formulated, they are introduced or administered into target cells. The administration is typically done as is known for the administration of nucleic acids into cells, and, as those skilled in the art will appreciate, the methods may depend on the choice of the target cell. Suitable methods include, but are not limited to, microinjection, electroporation, lipofection, etc. By "target cells" herein is meant prokaryotic or eukaryotic cells. Suitable prokaryotic cells include, but are not limited to, bacteria such as *E. coli*, Bacillus species, and the extremophile bacteria such as thermophiles, halophiles, etc. Preferably, the procaryotic target cells are recombination competent. Suitable eukaryotic cells include, but are not limited to, fungi such as yeast and filamentous fungi, including species of Aspergillus, Trichoderma, and Neurospora; plant cells including those of corn, sorghum, tobacco, canola, soybean, cotton, tomato, potato, alfalfa, sunflower, etc.; and animal cells, including fish, reptiles, amphibia, birds and mammals. Suitable fish cells include, but are not limited to, those from species of salmon, trout, tilapia, tuna, carp, flounder, halibut, swordfish, cod and zebrafish. Suitable bird cells include, but are not limited to, those of chickens, ducks, quail, pheasants, ostrich, and turkeys, and other jungle foul or game birds. Suitable mammalian cells include, but are not limited to, cells from horses, cows, buffalo, deer, sheep, rabbits, rodents such as mice, rats, hamsters and guinea pigs, goats, pigs, primates, marine mammals including dolphins and whales, as well as cell lines, such as human cell lines of any tissue or stem cell type, and stem cells, including pluripotent and non-pluripotent, and non-human zygotes. Particular human cells including, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells, osteoclasts, chondrocytes and other connective tissue cells, keratinocytes, melanocytes, liver cells, kidney cells, and adipocytes. Suitable cells also include known research cells, including, but not limited to, Jurkat T cells, mouse La, HT1080, C127, Rat2, CV-1, NIH3T3 cells, CHO, COS, 293 cells, etc. See the ATCC cell line catalog, hereby expressly incorporated by reference.

In a preferred embodiment, procaryotic cells are used to identify, clone, or alter gene family members. In this embodiment, a pre-selected target DNA sequence is chosen for alteration. Preferably, the pre-selected target DNA sequence is contained within an extrachromosomal sequence. By "extrachromosomal sequence" herein is meant a sequence separate from the chromosomal or genomic sequences. Preferred extrachromosomal sequences include plasmids (particularly procaryotic plasmids such as bacterial plasmids), p1 vectors, viral genomes, yeast, bacterial and mammalian artificial chromosomes (YAC, BAC and MAC, respectively), and other autonomously self-replicating sequences, although this is not required. As described herein, a recombinase and at least two single stranded targeting polynucleotides which are substantially complementary to each other, each of which contain a homology clamp to the target sequence contained on the extrachromosomal sequence, are added to the extrachromosomal sequence, preferably in vitro. The two single stranded targeting polynucleotides are preferably coated with recombinase, and at least one of the targeting polynucleotides contain at least one nucleotide substitution, insertion or deletion. The targeting polynucleotides then bind to the target sequence in the extrachromosomal sequence to effect homologous recombination and form an altered extrachromosomal sequence which contains the substitution, insertion or deletion. The altered extrachromosomal sequence is then introduced into the procaryotic cell using techniques known in the art. Preferably, the recombinase is removed prior to introduction into the target cell, using techniques known in the art. For example, the reaction may be treated with proteases such as proteinase K, detergents such as SDS, and phenol extraction (including phenol:chloroform:isoamyl alcohol extraction). These methods may also be used for eukaryotic cells.

Alternatively, the pre-selected target DNA sequence is a chromosomal sequence. In this embodiment, the recombinase with the targeting polynucleotides are introduced into the target cell, preferably eukaryotic target cells. In this embodiment, it may be desirable to bind (generally non-covalently) a nuclear localization signal to the targeting polynucleotides to facilitate localization of the complexes in the nucleus. See for example Kido et al., Exper. Cell Res. 198:107–114 (1992), hereby expressly incorporated by reference. The targeting polynucleotides and the recombinase function to effect homologous recombination, resulting in altered chromosomal or genomic sequences.

In a preferred embodiment, eukaryotic cells are used. For making transgenic non-human animals (which include homologously targeted non-human animals) embryonal stem cells (ES cells), donor cells for nuclear transfer and fertilized zygotes are preferred. In a preferred embodiment, embryonal stem cells are used. Murine ES cells, such as AB-1 line grown on mitotically inactive SNL76/7 cell feeder layers (McMahon and Bradley, Cell 62: 1073–1085 (1990)) essentially as described (Robertson, E. J. (1987) in *Teratocarcinomas and Embryonic Stem Cells: A Practical Approach*. E. J. Robertson, ed. (oxford: IRL Press), p. 71–112; Zjilstra et al., Nature 342:435–438 (1989); and Schwartzberg et al., Science 246:799–803 (1989), each of which is incorporated herein by reference) may be used for homologous gene targeting. Other suitable ES lines include, but are not limited to, the E14 line (Hooper et al. (1987) Nature 326: 292–295), the D3 line (Doetschman et al. (1985) J. Embryol. Exp. Morph. 87: 21–45), and the CCE line (Robertson et al. (1986) Nature 323: 445–448). The success of generating a mouse line from ES cells bearing a specific targeted mutation depends on the pluripotence of the ES cells (i.e., their ability, once injected into a host blastocyst, to participate in embryogenesis and contribute to the germ cells of the resulting animal).

The pluripotence of any given ES cell line can vary with time in culture and the care with which it has been handled. The only definitive assay for pluripotence is to determine whether the specific population of ES cells to be used for targeting can give rise to chimeras capable of germlne transmission of the ES genome. For this reason, prior to gene targeting, a portion of the parental population of AB-1 cells is injected into C57B1/6J blastocysts to ascertain whether the cells are capable of generating chimeric mice with extensive ES cell contribution and whether the majority of these chimeras can transmit the ES genome to progeny.

In a preferred embodiment, non-human zygotes are used, for example to make transgenic animals, using techniques known in the art (see U.S. Pat. No. 4,873,191; Brinster et al., PNAS 86:7007 (1989); Susulic et al., J. Biol. Chem. 49:29483 (1995), and Cavard et al., Nucleic Acids Res. 16:2099 (1988), hereby incorporated by reference). Preferred zygotes include, but are not limited to, animal zygotes, including fish, avian, reptilian, amphibian and mammalian zygotes. Suitable fish zygotes include, but are not limited to, those from species of salmon, trout, tuna, carp, flounder, halibut, swordfish, cod, tilapia and zebrafish. Suitable bird zygotes include, but are not limited to, those of chickens, ducks, quail, pheasant, turkeys, and other jungle fowl and game birds. Suitable mammalian zygotes include, but are not limited to, cells from horses, cows, buffalo, deer, sheep, rabbits, rodents such as mice, rats, hamsters and guinea pigs, goats, pigs, primates, and marine mammals including dolphins and whales. See Hogan et al., Manipulating the Mouse Embryo (A Laboratory Manual), 2nd Ed. Cold Spring Harbor Press, 1994, incorporated by reference.

The vectors containing the DNA segments of interest can be transferred into the host cell by well-known methods, depending on the type of cellular host. For example, microinjection is commonly utilized for target cells, although calcium phosphate treatment, electroporation, lipofection, biolistics or viral-based transfection also may be used. Other methods used to transform mammalian cells include the use of Polybrene, protoplast fusion, and others (see, generally, Sambrook et al. Molecular Cloning: A Laboratory Manual, 2d ed., 1989, Cold Spring Harbor Laboratory Press, Cold Spring Harbor, N.Y., which is incorporated herein by reference). Direct injection of DNA and/or recombinase-coated targeting polynucleotides into target cells, such as skeletal or muscle cells also may be used (Wolff et al. (1990) Science 247: 1465, which is incorporated herein by reference).

In a preferred embodiment, the precursor animals or cells already contain a disease allele. As used herein, the term "disease allele" refers to an allele of a gene which is capable of producing a recognizable disease. A disease allele may be dominant or recessive and may produce disease directly or when present in combination with a specific genetic background or pre-existing pathological condition. A disease allele may be present in the gene pool or may be generated de novo in an individual by somatic mutation. For example and not limitation, disease alleles include: activated oncogenes, a sickle cell anemia allele, a Tay-Sachs allele, a cystic fibrosis allele, a Lesch-Nyhan allele, a retinoblastoma-susceptibility allele, a Fabry's disease allele, a Huntington's chorea allele, and a xenoderma pigmentosa allele. As used herein, a disease allele encompasses both alleles associated with human diseases and alleles associated with recognized veterinary diseases. For example, the ΔAF508 CFTR allele in a human disease allele which is associated with cystic fibrosis in North Americans.

Once made and administered to target cells, new members of the gene family may be isolated as outlined herein.

Alternatively, the target cells may be screened to identify a cell that contains the targeted consensus functional domain sequence modification. This will be done in any number of ways, and will depend on the target gene and targeting polynucleotides as will be appreciated by those in the art. The screen may be based on phenotypic, biochemical, genotypic, or other functional changes, depending on the target sequence. For example, IgE levels may be evaluated for inflammation or asthma; vascular tone or blood pressure can be evaluated for hypertension, behavior screens can be done for neurologic effects, lipoprotein profiles can be screened for cardiovascular effects; secreted molecules can be evaluated for endocrine processes; CBCs can be done for hematology studies, etc. In an additional embodiment, as will be appreciated by those in the art, selectable markers or marker sequences may be included in the targeting polynucleotides to facilitate later identification.

In a preferred embodiment, kits containing the compositions of the invention are provided. The kits include the compositions, particularly those of libraries or pools of degenerate cssDNA probes, along with any number of reagents or buffers, including recombinases, buffers, salts, ATP, etc.

The broad scope of this invention is best understood with reference to the following examples, which are not intended to limit the invention in any manner. All references cited herein are expressly incorporated by reference. Although the present invention has been described in some detail by way of illustration for purposes of clarity of understanding, it will be apparent that certain changes and modifications may be practiced within the scope of the claims.

EXAMPLES

Example 1

Calcitonin Type GPCR Subfamily

A Calcitonin type GPCR subfamily serves as an example. The first consensus motif used is "TWDGW" (SEQ ID NO:7) for which degenerate oligonucleotide "ACNTGG-GAYGGNTGG" (SEQ ID NO:93) is synthesized. The second consensus motif is "GWGFP" (SEQ ID NO:11) for which antisense degenerate oligonucleotide "NGGRAANC-CCCANCC" (SEQ ID NO:94) is synthesized. The degeneracy of these oligos is 32 and 128 respectively, with each oligo containing a Biotin moity at the 5' end. cDNA or a cDNA library is used as a template for PCR amplification using described oligonucleotides as primers. The double stranded-amplified product is thermally denatured, cooled and coated with RecA as described. A CDNA library is used as substrate for targeting. After binding the specific target plasmid and washing away nonspecific sequences the bound material can be analyzed. Bound plasmids are transformed into E. coli cells with colony PCR performed using the original oligonucleotides as primers. This particular example should yield a PCR product of about 600 base pairs depending on the family member isolated. Other screening procedures can also be used including but not limited to hybridization to homologous probes, complementation of cells mutant for a family member, etc. Positive colonies (yielding efficient and specific amplification) are further analyzed by sequence to identify family members. The DNA sequences can then be reverse transcribed by computer analysis and compared to known protein sequences to determine if they represent known or novel family members.

Example 2

α2-Adrenergic Receptors

Adrenegic receptors play a prominent role in a wide variety of physiologicial processes (Kobilka, chapter 3). Examples of two well-characterized families of adrenergic receptors are the α2-adrenergic receptors (α2-ARs) and the β-adrenergic receptors (β-AR's). α2-AR's play a major role in the cardiovascular system and have profound, yet conflicting, effects on blood pressure. If α2-Ars are stimulated in the brainstem, blood pressure decreases, whereas if α2-AR's are stimulated in smooth muscle, blood pressure increases. The three subtypes of A2-AR's known to date, α2a α2b and α2c, show 50–60% homology to each other and may each contribute in differing degrees to these effects. Our current understanding of the role of each receptor subtype comes from the analysis of animal models in which each subtype was systematically knocked out. Link et al (1995,1996) show that stimulation of α2b receptors in vascular smooth muscle produced hypertension and counteracted the clinically beneficial hypotensive effect of stimulating α2a receptors in the central nervous system. Thus, knowledge of the specific role of each receptor subtype and its interaction with other family members is crucial to understanding the physiological significance of each as well as providing proper therapeutic treatments for disease states.

α2-ARs impact several different physiological systems including the cardiovascular system. There is a particular impact on vasoconstriction and vasodilabon and the concomitant regulation of blood pressure. Neural effects include such parameters as sypathetic outflow, sedation/anaesthesia and neurological modulation, metabolic effects such as decreased lipolysis, decreased insulin release, and stimulation of pitutatary GHRH release. Other miscellaneous effects such as inhibition of gastric motility and/or acid secretion, platelet aggregation and uterine contractibility. The affected systems allows for easy identification of HMT candidate animals. Microinjection of the consensus sequence (FIG. 1B; SEQ ID NOS:40–45) followed by screening the library of HMT mice having modifications in existing or new α2ARs. The screening is done using a variety of existing physiological assays such as blood pressure measurements. Knockout animals from known receptor subtypes, as well as new family members of specific classes of receptors advances the understanding of the biological mechanisms controlled by each.

Example 3

B-adrenergic Receptors

At least three distinct beta-adrenergic receptor (β-AR) subtypes exist in mammals, which modulate a wide variety of processes including cardiac function, development and behavior, metabolism and smooth muscle tone. These subtypes, β1, β2, and β3 adrenergic receptors, share the consensus sequence shown in FIG. 1B (SEQ ID NOS:46–48). While the β3 subtype appears to be primarily expressed in adipose tissue where it may regulate metabolic processes, the functional contributions specific to either the β1 or β2 receptor has proven to be more difficult to assess, as some tissues express both receptor subtypes and pharmacological agents used to dissect the relative contributions of different receptors are not always subtype-specific. Again, as with α2ARs, knockout systems have greatly increased our knowledge of subtype specific effects. Knockout animals have not only allowed assignation of function to individual subtypes but also serve as a test for functional redundancy between subtypes. Rohrer et al (1996) have shown that the mouse β1 receptor plays a role in development, and regulates the chronotropic and inotropic responses after administration of agonist. As described for α2-ARs, we can use similar phontypic screens to isolate, identify and determine function for members of the β-AR family.

Example 4

14-3-3 Proteins

A fundamental problem in drug discovery for cancer is that model systems are not predictive. Drug candidates are tested in animals carrying transplanted human tumors (xenografts), but very few drugs that show anticancer activity in xenografts have been successful in clinical trials. Furthermore, cancer is a polygenic disease; hence, it is difficult to produce transgenic animal models for cancer with single gene modifications.

Most cancers result from defects in DNA repair, cell cycle checkpoint and regulation or cell apoptosis. Members of the 14-3-3 family are involved in many of these pathways. For instance, 14-3-3 proteins are involved in cell cycle control. After DNA damage, 14-3-3 expression is increased by p53, this results in the binding of 14-3-3 protein to phosphorylated Cdc25C, which in turn results in the dephosphorylization or Cdc2, which finally causes the cell cycle to stop at G2 stage (Hermeking H., *Molecular Cell*, 1997, vol. 1, 3–11). 14-3-3 protein binds the phosphorylated BAD gene product, an agonist of apoptosis (Zha, J, *Cell*, 1996, vol. 87, 619–628; Zha J.,*J. Biol. Chem.*, 1997, vol. 272, 24101–24104). 14-3-3 proteins also regulate Raf, Cbl and other oncogene activities (Geoffrey, J., Clark, J., *Biol. Chem*, 1997, vol. 272, 20990–20993; Tzivion, G., *Nature*, 1998, vol. 394, 88–92). In addition, 14-3-3 protein expression is increased in bladder squamous cell carcinomas and lung tumor tissues (Ostergaard, M., *Cancer Res.*, 1997, vol. 57, 4111–4117; Nakanishi, K., *Hum Antibodies*, 1997, vol. 8,189–94).

Using 14-3-3 binding domains as a consense probe for HMT targeting, several genes in the 14-3-3 family can be knocked out or modified at the same time to generate cancer models. In the 14-3-3 gene family, the binding sites in 14-3-3 proteins are very conserved between species and various isoforms. This conservation is more than 90% at the amino acid level, and more than 70% at DNA sequence level (FIG. 4; SEQ ID NOS:62–77). Targeting probes designed to substitute two basic amino acids (R, K) with acidic amino acids (E,E) are shown in FIG. 5 (SEQ ID NOS:87–92). Recombinase proteins formulated with HMT probes allow toleration of 30% heterologous sequences for homologous recombination. This probe still has more than 70% homology to 14-3-3 family proteins, and it can target many 14-3-3 family genes.

HMT probes from the 14-3-3 gene family are introduced into normal mammalian cells, 14-3-3 targeted cells are screened by for cell transformation assays. To further validate if particular 14-3-3 targeted cells are important for cancerous phenotypes, targeted cells are transplanted into animals to test for tumor formation. The genotype of HMT targeted cells are characterized by PCR and Southern blotting.

When HMT probes from the 14-3-3 gene family are introduced into cells or zygotes used to produce transgenic animals, transgenic animal cancer models are screened by their sensitivity to tumor generating carcinogenic chemicals. Lung cancer models, transgenic mice are treated with urethane. In leukemia models, transgenic mice are treated with γ-irradiation. For other cancers, γ-irradiation or other tumor-generating chemicals are also to be used. The genotypes of HMT targeted animals are characterized by PCR and Southern blotting.

We claim:

1. A composition comprising:
   (a) a recombinase; and
   (b) a plurality of pairs of substantially complementary single-stranded targeting polynucleotides, wherein each pair comprises a nucleic acid sequence encoding a protein consensus sequence of a gene family, and wherein each pair has a consensus homology clamp substantially complementary to or substantially corresponding to at least a portion of said nucleic acid sequence encoding said protein consensus sequence.

2. The composition according to claim 1, wherein said gene family is selected from the group consisting of the G-protein coupled receptor family, the AAA-protein family, the bZIP transcription factor family, the mutS family, the recA family, the recF family, the Bcl-2 family, the single-stranded binding protein family; the TFIID transcription family, the TGF-beta family, the TNF family, the XPA family, the 14-3-3 family, and the XPG family.

3. The composition according to claim 1, wherein at least one of said polynucleotides further comprises an insertion sequence.

4. The composition according to claim 1, wherein at least one of said single-stranded targeting polynucleotides of each pair further comprises a purification tag.

5. The composition according to claim 1, wherein said targeting polynucleotides are coated with recombinase.

6. The composition according to claim 1, wherein said recombinase is a species of prokaryotic recombinase.

7. The composition according to claim 1, wherein said recombinase is a species of eukaryotic recombinase.

8. A kit comprising the composition of claim 1, and at least one reagent.

* * * * *

SEQUENCE LISTING

```
<160> NUMBER OF SEQ ID NOS: 95

<210> SEQ ID NO 1
<211> LENGTH: 5
<212> TYPE: PRT
<213> ORGANISM: Artificial Sequence
<220> FEATURE:
<221> NAME/KEY: MISC_FEATURE
<222> LOCATION: (4)
<223> OTHER INFORMATION: The amino acid at position 4 can be either
      Leucine or Phenylalanine.
<220> FEATURE:
<221> NAME/KEY: MISC_FEATURE
<222> LOCATION: (5)
<223> OTHER INFORMATION: The amino acid at position 5 can be either
      Tyrosine, Phenylalanine or Histidine.
<220> FEATURE:
<223> OTHER INFORMATION: Description of Artificial Sequence:  consensus
      sequence

<400> SEQUENCE: 1

Glu Ala Met Xaa Xaa
```

```
              1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence:  consensus
      sequence
<220> FEATURE:
<221> NAME/KEY: MISC_FEATURE
<222> LOCATION: (1)
<223> OTHER INFORMATION: The amino acid at position 1 can be either
      Tyrosine or Histidine.

<400> SEQUENCE: 2

Xaa Ala Leu Glu Gln
  1               5

<210> SEQ ID NO 3
<211> LENGTH: 5
<212> TYPE: PRT
<213> ORGANISM: Artificial Sequence
<220> FEATURE:
<221> NAME/KEY: MISC_FEATURE
<222> LOCATION: (5)
<223> OTHER INFORMATION: The amino acid at position 5 can be either
      Serine or Alanine.
<220> FEATURE:
<223> OTHER INFORMATION: Description of Artificial Sequence:  consensus
      sequence

<400> SEQUENCE: 3

Ile Pro Gln Ile Xaa
  1               5

<210> SEQ ID NO 4
<211> LENGTH: 5
<212> TYPE: PRT
<213> ORGANISM: Artificial Sequence
<220> FEATURE:
<221> NAME/KEY: MISC_FEATURE
<222> LOCATION: (4)
<223> OTHER INFORMATION: The amino acid at position 4 can be either
      Arginine or Cysteine.
<220> FEATURE:
<223> OTHER INFORMATION: Description of Artificial Sequence:  consensus
      sequence

<400> SEQUENCE: 4

Lys Thr Asn Xaa Ile
  1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 5

Phe Asn Glu Ala Lys
  1               5

<210> SEQ ID NO 6
<211> LENGTH: 6
<212> TYPE: PRT
<213> ORGANISM: Artificial Sequence
<220> FEATURE:
```

```
<223> OTHER INFORMATION: Description of Artificial Sequence:  consensus
      sequence

<400> SEQUENCE: 6

Phe Thr Met Tyr Thr Thr
 1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 7

Thr Trp Asp Gly Trp
 1               5

<210> SEQ ID NO 8
<211> LENGTH: 6
<212> TYPE: PRT
<213> ORGANISM: Artificial Sequence
<220> FEATURE:
<221> NAME/KEY: MISC_FEATURE
<222> LOCATION: (3)
<223> OTHER INFORMATION: The amino acid at position 3 can be either
      Proline or Glutamine.
<220> FEATURE:
<223> OTHER INFORMATION: Description of Artificial Sequence:  consensus
      sequence

<400> SEQUENCE: 8

Tyr Phe Xaa Asp Phe Asp
 1               5

<210> SEQ ID NO 9
<211> LENGTH: 5
<212> TYPE: PRT
<213> ORGANISM: Artificial Sequence
<220> FEATURE:
<221> NAME/KEY: MISC_FEATURE
<222> LOCATION: (4)
<223> OTHER INFORMATION: The amino acid at position 4 can be either
      Valin  or Isoleucine.
<220> FEATURE:
<223> OTHER INFORMATION: Description of Artificial Sequence:  consensus
      sequence

<400> SEQUENCE: 9

Cys Gln Arg Xaa Thr
 1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 10

Cys Tyr Asn Phe Trp Met
 1               5

<210> SEQ ID NO 11
<211> LENGTH: 5
<212> TYPE: PRT
<213> ORGANISM: Artificial Sequence
```

```
<220> FEATURE:
<223> OTHER INFORMATION: Description of Artificial Sequence:  consensus
      sequence

<400> SEQUENCE: 11

Gly Trp Gly Phe Pro
 1               5

<210> SEQ ID NO 12
<211> LENGTH: 6
<212> TYPE: PRT
<213> ORGANISM: Artificial Sequence
<220> FEATURE:
<221> NAME/KEY: MISC_FEATURE
<222> LOCATION: (6)
<223> OTHER INFORMATION: The amino acid at position 6 can be either
      Leucine, Methionine or Isoleucine.
<220> FEATURE:
<223> OTHER INFORMATION: Description of Artificial Sequence:  consensus
      sequence

<400> SEQUENCE: 12

Asn Asp Asn Cys Trp Xaa
 1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 13

Tyr Ile Ile His Gly Pro
 1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 14

Trp Tyr Leu Pro Trp
 1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 15

Tyr Thr Val Gly Tyr
 1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence:  consensus
      sequence
```

```
<400> SEQUENCE: 16

His Cys Thr Arg Asn
 1               5

<210> SEQ ID NO 17
<211> LENGTH: 5
<212> TYPE: PRT
<213> ORGANISM: Artificial Sequence
<220> FEATURE:
<221> NAME/KEY: MISC_FEATURE
<222> LOCATION: (2)
<223> OTHER INFORMATION: The amino acid at position 2 can be either
      Lysin  or Asparagine.
<220> FEATURE:
<223> OTHER INFORMATION: Description of Artificial Sequence:  consensus
      sequence

<400> SEQUENCE: 17

Asn Xaa Glu Val Gln
 1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 18

Lys Leu His Cys Thr
 1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 19

Val Glu Gly Leu Tyr Leu
 1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 20

Tyr Cys Phe Leu Asn
 1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 21

Tyr Asp Phe Asn His Lys
 1               5
```

```
<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: consensus
      sequence

<400> SEQUENCE: 22

Thr Trp Ala Asn Tyr
  1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: consensus
      sequence

<400> SEQUENCE: 23

Tyr Thr Val Gly Tyr
  1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: consensus
      sequence

<400> SEQUENCE: 24

Asn Tyr Tyr Trp Ile Leu
  1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: consensus
      sequence

<400> SEQUENCE: 25

Phe Gly Val His Tyr
  1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: consensus
      sequence

<400> SEQUENCE: 26

Phe Gln Gly Phe Phe Val
  1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: consensus
      sequence
```

```
<400> SEQUENCE: 27

Cys Asn Gly Glu Val Gln
  1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: consensus
      sequence

<400> SEQUENCE: 28

Val Asn Asn Tyr Phe Leu
  1               5

<210> SEQ ID NO 29
<211> LENGTH: 5
<212> TYPE: PRT
<213> ORGANISM: Artificial Sequence
<220> FEATURE:
<221> NAME/KEY: MISC_FEATURE
<222> LOCATION: (4)
<223> OTHER INFORMATION: The amino acid at position 4 can be either
      Phenyalanine or Tyrosine.
<220> FEATURE:
<223> OTHER INFORMATION: Description of Artificial Sequence: consensus
      sequence

<400> SEQUENCE: 29

Met Asn Leu Xaa Thr
  1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: consensus
      sequence

<400> SEQUENCE: 30

Cys Asp Leu Trp Leu
  1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: consensus
      sequence

<400> SEQUENCE: 31

Asn Ala Ser Val Met Asn
  1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: consensus
      sequence

<400> SEQUENCE: 32

Trp Ala Pro Ala Ile
```

```
                              1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 33

Thr Phe Gly Thr Ala
  1               5

<210> SEQ ID NO 34
<211> LENGTH: 5
<212> TYPE: PRT
<213> ORGANISM: Artificial Sequence
<220> FEATURE:
<221> NAME/KEY: MISC_FEATURE
<222> LOCATION: (2)
<223> OTHER INFORMATION: The amino acid at position 2 can be either
      Threonine or Alanine.
<220> FEATURE:
<223> OTHER INFORMATION: Description of Artificial Sequence:  consensus
      sequence

<400> SEQUENCE: 34

Trp Xaa Pro Tyr Asn
  1               5

<210> SEQ ID NO 35
<211> LENGTH: 5
<212> TYPE: PRT
<213> ORGANISM: Artificial Sequence
<220> FEATURE:
<221> NAME/KEY: MISC_FEATURE
<222> LOCATION: (5)
<223> OTHER INFORMATION: The amino acid at position 5 can be either
      Phenylalanine or Leucine.
<220> FEATURE:
<223> OTHER INFORMATION: Description of Artificial Sequence:  consensus
      sequence

<400> SEQUENCE: 35

Thr Ala Ser Ile Xaa
  1               5

<210> SEQ ID NO 36
<211> LENGTH: 5
<212> TYPE: PRT
<213> ORGANISM: Artificial Sequence
<220> FEATURE:
<221> NAME/KEY: MISC_FEATURE
<222> LOCATION: (2)
<223> OTHER INFORMATION: The amino acid at position 2 can be either
      Alanine or Glycine.
<220> FEATURE:
<223> OTHER INFORMATION: Description of Artificial Sequence:  consensus
      sequence

<400> SEQUENCE: 36

Met Xaa Ala Phe Ile
  1               5

<210> SEQ ID NO 37
<211> LENGTH: 6
<212> TYPE: PRT
<213> ORGANISM: Artificial Sequence
<220> FEATURE:
```

```
<221> NAME/KEY: MISC_FEATURE
<222> LOCATION: (3)
<223> OTHER INFORMATION: The amino acid at position 3 can be either
      Isoleucine or Phenyalanine.
<220> FEATURE:
<223> OTHER INFORMATION: Description of Artificial Sequence:  consensus
      sequence

<400> SEQUENCE: 37

Cys Trp Xaa Pro Tyr Phe
  1               5

<210> SEQ ID NO 38
<211> LENGTH: 5
<212> TYPE: PRT
<213> ORGANISM: Artificial Sequence
<220> FEATURE:
<221> NAME/KEY: MISC_FEATURE
<222> LOCATION: (3)..(4)
<223> OTHER INFORMATION: The amino acid at positions 3 and 4 can be
      either Valine or Isoleucine.
<220> FEATURE:
<223> OTHER INFORMATION: Description of Artificial Sequence:  consensus
      sequence

<400> SEQUENCE: 38

Ile Phe Xaa Xaa Gly
  1               5

<210> SEQ ID NO 39
<211> LENGTH: 5
<212> TYPE: PRT
<213> ORGANISM: Artificial Sequence
<220> FEATURE:
<221> NAME/KEY: MISC_FEATURE
<222> LOCATION: (3)
<223> OTHER INFORMATION: The amino acid at position 3 can be either
      Isoleucine or Leucine.
<220> FEATURE:
<221> NAME/KEY: MISC_FEATURE
<222> LOCATION: (4)
<223> OTHER INFORMATION: The amino acid at position 4 can be either
      Leucine or Valine.
<220> FEATURE:
<223> OTHER INFORMATION: Description of Artificial Sequence:  consensus
      sequence

<400> SEQUENCE: 39

Lys Asn Xaa Xaa Gly
  1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 40

Ala Pro Gln Asn Leu Phe
  1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence:  consensus
      sequence
```

```
<400> SEQUENCE: 41

Ala Asp Ile Leu Val
 1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 42

Tyr Leu Ala Leu Asp
 1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 43

Phe Phe Ala Pro Cys
 1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 44

Phe Thr Phe Val Leu Ala
 1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 45

Cys Trp Phe Pro Phe Phe Phe
 1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 46

Asp Val Leu Cys Val Thr
 1               5

<210> SEQ ID NO 47
<211> LENGTH: 6
<212> TYPE: PRT
```

```
<213> ORGANISM: Artificial Sequence
<220> FEATURE:
<223> OTHER INFORMATION: Description of Artificial Sequence: consensus
      sequence

<400> SEQUENCE: 47

Phe Thr Leu Cys Trp Leu
 1               5

<210> SEQ ID NO 48
<211> LENGTH: 5
<212> TYPE: PRT
<213> ORGANISM: Artificial Sequence
<220> FEATURE:
<221> NAME/KEY: MISC_FEATURE
<222> LOCATION: (1)
<223> OTHER INFORMATION: The amino acid at position 1 can be either
      Alanine or Glycine.
<220> FEATURE:
<221> NAME/KEY: MISC_FEATURE
<222> LOCATION: (5)
<223> OTHER INFORMATION: The amino acid at position 5 can be either
      Leucine or Isoleucine.
<220> FEATURE:
<223> OTHER INFORMATION: Description of Artificial Sequence: consensus
      sequence

<400> SEQUENCE: 48

Xaa Phe Asn Pro Xaa
 1               5

<210> SEQ ID NO 49
<211> LENGTH: 5
<212> TYPE: PRT
<213> ORGANISM: Artificial Sequence
<220> FEATURE:
<221> NAME/KEY: MISC_FEATURE
<222> LOCATION: (5)
<223> OTHER INFORMATION: The amino acid at position 5 can be either
      Phenyalanine, Isoleucine, Leucine or Valine.
<220> FEATURE:
<223> OTHER INFORMATION: Description of Artificial Sequence: consensus
      sequence

<400> SEQUENCE: 49

Gly Lys Thr Gln Xaa
 1               5

<210> SEQ ID NO 50
<211> LENGTH: 5
<212> TYPE: PRT
<213> ORGANISM: Artificial Sequence
<220> FEATURE:
<221> NAME/KEY: MISC_FEATURE
<222> LOCATION: (1)
<223> OTHER INFORMATION: The amino acid at position 1 can be either
      Isoleucine, Leucine or Methionine.
<220> FEATURE:
<221> NAME/KEY: MISC_FEATURE
<222> LOCATION: (2)
<223> OTHER INFORMATION: The amino acid at position 2 can be either
      Phenyalanine or Tyrosine.
<220> FEATURE:
<221> NAME/KEY: MISC_FEATURE
<222> LOCATION: (5)
<223> OTHER INFORMATION: The amino acid at position 5 can be either
      Threonine or Serine.
<220> FEATURE:
<223> OTHER INFORMATION: Description of Artificial Sequence: consensus
      sequence

<400> SEQUENCE: 50
```

```
Xaa Xaa Ile Asp Xaa
 1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 51

Lys Asn Arg Glu Ala Ala
 1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 52

Cys Arg Lys Arg Lys
 1               5

<210> SEQ ID NO 53
<211> LENGTH: 5
<212> TYPE: PRT
<213> ORGANISM: Artificial Sequence
<220> FEATURE:
<221> NAME/KEY: MISC_FEATURE
<222> LOCATION: (2)
<223> OTHER INFORMATION: The amino acid at position 2 can be either
      Isoleucine or Valine.
<220> FEATURE:
<221> NAME/KEY: MISC_FEATURE
<222> LOCATION: (3)
<223> OTHER INFORMATION: The amino acid at position 3 can be either
      Lysin  or Threonine.
<220> FEATURE:
<223> OTHER INFORMATION: Description of Artificial Sequence:  consensus
      sequence

<400> SEQUENCE: 53

Trp Xaa Xaa Gln Pro
 1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 54

Gly Pro Asn Met Gly Gly
 1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 55
```

```
Asp Glu Leu Gly Arg
 1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 56

Gly Phe Arg Gly Glu Ala
 1               5

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 57

Phe Ala Asp Ile Gly Trp
 1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 58

His Glu Leu Tyr Val
 1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 59

Gly Trp Asn Asp Trp Ile Val
 1               5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 60

Asp Leu Gly Trp Lys Trp
 1               5

<210> SEQ ID NO 61
<211> LENGTH: 6
<212> TYPE: PRT
<213> ORGANISM: Artificial Sequence
```

```
<220> FEATURE:
<221> NAME/KEY: MISC_FEATURE
<222> LOCATION: (6)
<223> OTHER INFORMATION: The amino acid at position 6 can be either
      Threonine or Cysteine.
<220> FEATURE:
<223> OTHER INFORMATION: Description of Artificial Sequence:  consensus
      sequence

<400> SEQUENCE: 61

Gly Ser Asp Asp Tyr Xaa
  1               5

<210> SEQ ID NO 62
<211> LENGTH: 43
<212> TYPE: PRT
<213> ORGANISM: Homo sapiens

<400> SEQUENCE: 62

Ile Arg Leu Gly Leu Ala Leu Asn Phe Ser Val Phe Tyr Tyr Glu Ile
  1               5                  10                  15

Gln Asn Ala Pro Glu Gln Ala Cys Leu Leu Ala Lys Gln Ala Phe Asp
             20                  25                  30

Asp Ala Ile Ala Glu Leu Asp Thr Leu Asn Glu
         35                  40

<210> SEQ ID NO 63
<211> LENGTH: 43
<212> TYPE: PRT
<213> ORGANISM: Homo sapiens

<400> SEQUENCE: 63

Ile Arg Leu Gly Leu Ala Leu Asn Phe Ser Val Phe Tyr Tyr Glu Ile
  1               5                  10                  15

Leu Asn Ser Pro Glu Lys Ala Cys Ser Leu Ala Lys Thr Ala Phe Asp
             20                  25                  30

Glu Ala Ile Ala Glu Leu Asp Thr Leu Asn Glu
         35                  40

<210> SEQ ID NO 64
<211> LENGTH: 43
<212> TYPE: PRT
<213> ORGANISM: Homo sapiens

<400> SEQUENCE: 64

Ile Arg Leu Gly Leu Ala Leu Asn Phe Ser Val Phe Tyr Tyr Glu Ile
  1               5                  10                  15

Leu Asn Asn Pro Glu Leu Ala Cys Thr Leu Ala Lys Thr Ala Phe Asp
             20                  25                  30

Glu Ala Ile Ala Glu Leu Asp Thr Leu Asn Glu
         35                  40

<210> SEQ ID NO 65
<211> LENGTH: 43
<212> TYPE: PRT
<213> ORGANISM: Homo sapiens

<400> SEQUENCE: 65

Ile Arg Leu Gly Leu Ala Leu Asn Phe Ser Val Phe Tyr Tyr Glu Ile
  1               5                  10                  15

Leu Asn Ser Pro Asp Arg Ala Cys Arg Leu Ala Lys Ala Ala Phe Asp
             20                  25                  30
```

```
Asp Ala Ile Ala Glu Leu Asp Thr Leu Ser Glu
         35                  40
```

<210> SEQ ID NO 66
<211> LENGTH: 43
<212> TYPE: PRT
<213> ORGANISM: Homo sapiens

<400> SEQUENCE: 66

```
Ile Arg Leu Gly Leu Ala Leu Asn Phe Ser Val Phe His Tyr Glu Ile
 1               5                  10                  15
Ala Asn Ser Pro Glu Glu Ala Ile Ser Leu Ala Lys Thr Thr Phe Asp
                20                  25                  30
Glu Ala Met Ala Asp Leu His Thr Leu Ser Glu
         35                  40
```

<210> SEQ ID NO 67
<211> LENGTH: 43
<212> TYPE: PRT
<213> ORGANISM: Homo sapiens

<400> SEQUENCE: 67

```
Ile Arg Leu Gly Leu Ala Leu Asn Phe Ser Val Phe Tyr Tyr Glu Ile
 1               5                  10                  15
Leu Asn Ser Pro Asp Arg Ala Cys Arg Leu Ala Lys Ala Ala Phe Asp
                20                  25                  30
Asp Ala Ile Ala Glu Leu Asp Thr Leu Ser Glu
         35                  40
```

<210> SEQ ID NO 68
<211> LENGTH: 43
<212> TYPE: PRT
<213> ORGANISM: Rat

<400> SEQUENCE: 68

```
Ile Arg Leu Gly Leu Ala Leu Asn Phe Ser Val Phe Tyr Tyr Glu Ile
 1               5                  10                  15
Gln Asn Ala Pro Glu Gln Ala Cys Leu Leu Ala Lys Gln Ala Phe Asp
                20                  25                  30
Asp Ala Ile Ala Glu Leu Asp Thr Leu Asn Glu
         35                  40
```

<210> SEQ ID NO 69
<211> LENGTH: 43
<212> TYPE: PRT
<213> ORGANISM: Rat

<400> SEQUENCE: 69

```
Ile Arg Leu Gly Leu Ala Leu Asn Phe Ser Val Phe Tyr Tyr Glu Ile
 1               5                  10                  15
Leu Asn Ser Pro Glu Lys Ala Cys Ser Leu Ala Lys Thr Ala Phe Asp
                20                  25                  30
Glu Ala Ile Ala Glu Leu Asp Thr Leu Asn Glu
         35                  40
```

<210> SEQ ID NO 70
<211> LENGTH: 43
<212> TYPE: PRT
<213> ORGANISM: Rat

<400> SEQUENCE: 70

```
Ile Arg Leu Gly Leu Ala Leu Asn Phe Ser Val Phe Tyr Tyr Glu Ile
 1               5                  10                  15

Leu Asn Asn Pro Glu Leu Ala Cys Thr Leu Ala Lys Thr Ala Phe Asp
                 20                  25                  30

Glu Ala Ile Ala Glu Leu Asp Thr Leu Asn Glu
                35                  40
```

<210> SEQ ID NO 71
<211> LENGTH: 43
<212> TYPE: PRT
<213> ORGANISM: Rat

<400> SEQUENCE: 71

```
Ile Arg Leu Gly Leu Ala Leu Asn Tyr Ser Val Phe Tyr Tyr Glu Ile
 1               5                  10                  15

Gln Asn Ala Pro Glu Gln Ala Cys His Leu Ala Lys Thr Ala Phe Asp
                 20                  25                  30

Asp Ala Ile Ala Glu Leu Asp Thr Leu Asn Glu
                35                  40
```

<210> SEQ ID NO 72
<211> LENGTH: 43
<212> TYPE: PRT
<213> ORGANISM: Rat

<400> SEQUENCE: 72

```
Ile Arg Leu Gly Leu Ala Leu Asn Phe Ser Val Phe Tyr Tyr Glu Ile
 1               5                  10                  15

Leu Asn Ser Pro Glu Lys Ala Cys Ser Leu Ala Lys Thr Ala Phe Asp
                 20                  25                  30

Glu Ala Ile Ala Glu Leu Asp Thr Leu Ser Glu
                35                  40
```

<210> SEQ ID NO 73
<211> LENGTH: 43
<212> TYPE: PRT
<213> ORGANISM: Bovine
<220> FEATURE:
<223> OTHER INFORMATION: Description of Artificial Sequence: synthetic

<400> SEQUENCE: 73

```
Ile Arg Leu Gly Leu Ala Leu Asn Phe Ser Val Phe Tyr Tyr Glu Ile
 1               5                  10                  15

Gln Asn Ala Pro Glu Gln Ala Cys Leu Leu Ala Lys Gln Ala Phe Asp
                 20                  25                  30

Asp Ala Ile Ala Glu Leu Asp Thr Leu Asn Glu
                35                  40
```

<210> SEQ ID NO 74
<211> LENGTH: 43
<212> TYPE: PRT
<213> ORGANISM: Bovine
<220> FEATURE:
<223> OTHER INFORMATION: Description of Artificial Sequence: synthetic

<400> SEQUENCE: 74

```
Ile Arg Leu Gly Leu Ala Leu Asn Phe Ser Val Phe Tyr Tyr Glu Ile
 1               5                  10                  15

Leu Asn Ser Pro Glu Lys Ala Cys Ser Leu Ala Lys Thr Ala Phe Asp
                 20                  25                  30

Glu Ala Ile Ala Glu Leu Asp Thr Leu Asn Glu
```

```
                35                  40

<210> SEQ ID NO 75
<211> LENGTH: 43
<212> TYPE: PRT
<213> ORGANISM: Bovine

<400> SEQUENCE: 75

Ile Arg Leu Gly Leu Ala Leu Asn Tyr Ser Val Phe Tyr Tyr Glu Ile
 1               5                  10                  15

Gln Asn Ala Pro Glu Gln Ala Cys His Leu Ala Lys Thr Ala Phe Asp
            20                  25                  30

Asp Ala Ile Ala Glu Leu Asp Thr Leu Asn Glu
        35                  40

<210> SEQ ID NO 76
<211> LENGTH: 43
<212> TYPE: PRT
<213> ORGANISM: Bovine

<400> SEQUENCE: 76

Ile Arg Leu Gly Leu Ala Leu Asn Phe Ser Val Phe Tyr Tyr Glu Ile
 1               5                  10                  15

Leu Asn Ser Pro Asp Arg Ala Cys Arg Leu Ala Lys Ala Ala Phe Asp
            20                  25                  30

Asp Ala Ile Ala Glu Leu Asp Thr Leu Ser Glu
        35                  40

<210> SEQ ID NO 77
<211> LENGTH: 43
<212> TYPE: PRT
<213> ORGANISM: Bovine

<400> SEQUENCE: 77

Ile Arg Leu Gly Leu Ala Leu Asn Phe Ser Val Phe Tyr Tyr Glu Ile
 1               5                  10                  15

Leu Asn Ala Pro Glu Lys Ala Cys Ser Leu Ala Lys Gln Ala Phe Asp
            20                  25                  30

Glu Ala Ile Ala Glu Leu Asp Thr Leu Ser Glu
        35                  40

<210> SEQ ID NO 78
<211> LENGTH: 43
<212> TYPE: PRT
<213> ORGANISM: Artificial Sequence
<220> FEATURE:
<221> NAME/KEY: MISC_FEATURE
<222> LOCATION: (2)
<223> OTHER INFORMATION: The amino acid at position 2 can be either
      Arginine or Glutamic acid.
<220> FEATURE:
<221> NAME/KEY: MISC_FEATURE
<222> LOCATION: (28)
<223> OTHER INFORMATION: The amino acid at position 28 can be either
      Lysin  or Glutamic acid.
<220> FEATURE:
<223> OTHER INFORMATION: Description of Artificial Sequence:  consensus
      sequence

<400> SEQUENCE: 78

Ile Xaa Leu Gly Leu Ala Leu Asn Phe Ser Val Phe Tyr Tyr Glu Ile
 1               5                  10                  15

Gln Asn Ala Pro Glu Gln Ala Cys Leu Leu Ala Xaa Gln Ala Phe Asp
            20                  25                  30
```

Asp Ala Ile Ala Glu Leu Asp Thr Leu Asn Glu
          35                  40

<210> SEQ ID NO 79
<211> LENGTH: 14
<212> TYPE: DNA
<213> ORGANISM: Artificial Sequence
<220> FEATURE:
<221> NAME/KEY: MISC_FEATURE
<222> LOCATION: (6)
<223> OTHER INFORMATION: "n" at position 6 can be any base.
<220> FEATURE:
<221> NAME/KEY: MISC_FEATURE
<222> LOCATION: (12)
<223> OTHER INFORMATION: "n" at position 12 can be any base.
<220> FEATURE:
<223> OTHER INFORMATION: Description of Artificial Sequence: synthetic

<400> SEQUENCE: 79
gargcnatgy tnyw                                                    14

<210> SEQ ID NO 80
<211> LENGTH: 15
<212> TYPE: DNA
<213> ORGANISM: Artificial Sequence
<220> FEATURE:
<221> NAME/KEY: MISC_FEATURE
<222> LOCATION: (12)
<223> OTHER INFORMATION: "n" at position 12 can be any base.
<220> FEATURE:
<223> OTHER INFORMATION: Description of Artificial Sequence: synthetic

<400> SEQUENCE: 80
ttyaaygarg cnaar                                                   15

<210> SEQ ID NO 81
<211> LENGTH: 17
<212> TYPE: DNA
<213> ORGANISM: Artificial Sequence
<220> FEATURE:
<221> NAME/KEY: MISC_FEATURE
<222> LOCATION: (6)
<223> OTHER INFORMATION: "n" at position 6 can be any base.
<220> FEATURE:
<221> NAME/KEY: MISC_FEATURE
<222> LOCATION: (15)
<223> OTHER INFORMATION: "n" at position 15 can be any base.
<220> FEATURE:
<223> OTHER INFORMATION: Description of Artificial Sequence: synthetic

<400> SEQUENCE: 81
ttyacnatgt ayacnac                                                 17

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence: synthetic

<400> SEQUENCE: 82
tgytayaayt tytggatg                                                18

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: synthetic

<400> SEQUENCE: 83
taygayttya aycayaar                                                18

<210> SEQ ID NO 84
<211> LENGTH: 17
<212> TYPE: DNA
<213> ORGANISM: Artificial Sequence
<220> FEATURE:
<221> NAME/KEY: MISC_FEATURE
<222> LOCATION: (3)
<223> OTHER INFORMATION: "n" at position 3 can be any base.
<220> FEATURE:
<223> OTHER INFORMATION: Description of Artificial Sequence: synthetic

<400> SEQUENCE: 84
gtnaayaayt ayttyyt                                                 17

<210> SEQ ID NO 85
<211> LENGTH: 14
<212> TYPE: DNA
<213> ORGANISM: Artificial Sequence
<220> FEATURE:
<223> OTHER INFORMATION: Description of Artificial Sequence: synthetic
<220> FEATURE:
<221> NAME/KEY: MISC_FEATURE
<222> LOCATION: (3)
<223> OTHER INFORMATION: "n" at position 3 can be any base.

<400> SEQUENCE: 85
htntwyathg ayws                                                    14

<210> SEQ ID NO 86
<211> LENGTH: 18
<212> TYPE: DNA
<213> ORGANISM: Artificial Sequence
<220> FEATURE:
<221> NAME/KEY: MISC_FEATURE
<222> LOCATION: (12)
<223> OTHER INFORMATION: "n" at position 12 can be any base.
<220> FEATURE:
<223> OTHER INFORMATION: Description of Artificial Sequence: synthetic

<400> SEQUENCE: 86
tgytggwthc cntaytty                                                18

<210> SEQ ID NO 87
<211> LENGTH: 129
<212> TYPE: DNA
<213> ORGANISM: Homo sapiens

<400> SEQUENCE: 87
atcagactgg gtctggccct taacttctct gtgttctatt atgagattct gaactcccca    60
gagaaagcct gctctcttgc aaagacagct tttgatgaag ccattgctga acttgataca   120
ttaagtgaa                                                          129

<210> SEQ ID NO 88
<211> LENGTH: 129
<212> TYPE: DNA
<213> ORGANISM: Homo sapiens

<400> SEQUENCE: 88
atccgcctgg gcctggccct gaactttttcc gtcttccact acgagatcgc caacagcccc   60
gaggaggcca tctctctggc caagaccact ttcgacgagg ccatggctga tctgcacacc   120
ctcagcgag                                                                129

<210> SEQ ID NO 89
<211> LENGTH: 129
<212> TYPE: DNA
<213> ORGANISM: Homo sapiens

<400> SEQUENCE: 89
atccggctgg gcctggccct caacttctcc gtgttctact atgagatcca gaatgcacct        60
gagcaagcct gcctcttagc caaacaagcc ttcgatgatg ccatagctga gctggacaca      120
ctaaacgag                                                                129

<210> SEQ ID NO 90
<211> LENGTH: 129
<212> TYPE: DNA
<213> ORGANISM: Homo sapiens

<400> SEQUENCE: 90
attcgtcttg gtctggcact aaattttcta gtcttttact atgagattct aaactctcct        60
gaaaaggcct gtagcctggc aaaaacggca tttgatgaag caattgctga attggatacg      120
ctgaatgaa                                                                129

<210> SEQ ID NO 91
<211> LENGTH: 129
<212> TYPE: DNA
<213> ORGANISM: Homo sapiens

<400> SEQUENCE: 91
attcgcttag gtcttgctct caattttcc gtattctact acgaaattct taattcccct         60
gaccgtgcct gcaggttggc aaaagcagct tttgatgatg caattgcaga actggatacg      120
ctgagtgaa                                                                129

<210> SEQ ID NO 92
<211> LENGTH: 129
<212> TYPE: DNA
<213> ORGANISM: Homo sapiens

<400> SEQUENCE: 92
atccgcctgg ggcttgctct taacttttct gtattttact atgagattct aataaccca         60 gagcttgcct gcacgctggc taaaacggct tttgatgagg ccattgctga acttgataca      120
ctgaatgaa                                                                129

<210> SEQ ID NO 93
<211> LENGTH: 15
<212> TYPE: DNA
<213> ORGANISM: Artificial Sequence
<220> FEATURE:
<221> NAME/KEY: MISC_FEATURE
<222> LOCATION: (3)
<223> OTHER INFORMATION: "n" at position 3 can be any base.
<220> FEATURE:
<221> NAME/KEY: MISC_FEATURE
<222> LOCATION: (12)
<223> OTHER INFORMATION: "n" at position 12 can be any base.
<220> FEATURE:
<223> OTHER INFORMATION: Description of Artificial Sequence: consensus
      sequence

<400> SEQUENCE: 93
acntgggayg gntgg                                                          15

```
<210> SEQ ID NO 94
<211> LENGTH: 15
<212> TYPE: DNA
<213> ORGANISM: Artificial Sequence
<220> FEATURE:
<221> NAME/KEY: MISC_FEATURE
<222> LOCATION: (1)
<223> OTHER INFORMATION: "n" at position 1 can be any base.
<220> FEATURE:
<221> NAME/KEY: MISC_FEATURE
<222> LOCATION: (7)
<223> OTHER INFORMATION: "n" at position 7 can be any base.
<220> FEATURE:
<221> NAME/KEY: MISC_FEATURE
<222> LOCATION: (13)
<223> OTHER INFORMATION: "n" at position 13 can be any base.
<220> FEATURE:
<223> OTHER INFORMATION: Description of Artificial Sequence:  consensus
      sequence

<400> SEQUENCE: 94
nggraanccc cancc                                                     15

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence:  consensus
      sequence

<400> SEQUENCE: 95

Gly Phe Arg Gly Glu Ala Leu
 1               5
```